(12) United States Patent
Yang

(10) Patent No.: US 7,326,728 B2
(45) Date of Patent: Feb. 5, 2008

(54) MODULATORS OF GLUCOCORTICOID RECEPTOR, AP-1, AND/OR NF-κβ ACTIVITY AND USE THEREOF

(75) Inventor: Bingwei Vera Yang, Belle Mead, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 207 days.

(21) Appl. No.: 11/035,119

(22) Filed: Jan. 13, 2005

(65) Prior Publication Data

US 2005/0182110 A1 Aug. 18, 2005

Related U.S. Application Data

(60) Provisional application No. 60/537,470, filed on Jan. 16, 2004.

(51) Int. Cl.
*A61K 31/426* (2006.01)
*C07D 277/38* (2006.01)

(52) U.S. Cl. .................. 514/371; 548/195; 548/332.5; 546/63; 546/270.7; 546/274.7; 514/286; 514/341; 514/342; 514/398

(58) Field of Classification Search ................ 514/371, 514/398, 342, 341, 286; 548/195, 332.5; 546/63, 270.7, 274.7
See application file for complete search history.

(56) References Cited

U.S. PATENT DOCUMENTS

| | | | |
|---|---|---|---|
| 3,517,073 A | 6/1970 | Fields | |
| 4,786,646 A | 11/1988 | Guthrie et al. | |
| 5,055,468 A | 10/1991 | Gray et al. | |
| 5,202,486 A | 4/1993 | Barrish et al. | |
| 5,332,820 A | 7/1994 | Duncia | |
| 5,409,932 A | 4/1995 | Schwenner et al. | |
| 5,411,960 A | 5/1995 | Schwenner et al. | |
| 5,455,248 A | 10/1995 | DeHaven-Hudkins et al. | |
| 5,514,683 A | 5/1996 | Kalindjian et al. | |
| 5,569,655 A | 10/1996 | Dority, Jr. et al. | |
| 5,616,780 A | 4/1997 | Pitteloud et al. | |
| 6,214,915 B1 | 4/2001 | Avakian et al. | |
| 6,262,059 B1 | 7/2001 | Pamukcu et al. | |
| 6,291,679 B1 | 9/2001 | Mailliet et al. | |
| 6,995,181 B2 | 2/2006 | Vaccaro et al. | |
| 2004/0132758 A1 | 7/2004 | Vaccaro et al. | |
| 2005/0171136 A1 | 8/2005 | Vaccaro et al. | |
| 2005/0176716 A1 | 8/2005 | Duan et al. | |
| 2005/0176749 A1 | 8/2005 | Yang | |
| 2005/0182082 A1 | 8/2005 | Duan et al. | |
| 2005/0182083 A1 | 8/2005 | Weinstein et al. | |
| 2005/0187242 A1 | 8/2005 | Weinstein et al. | |
| 2006/0154962 A1 | 7/2006 | Yang | |
| 2006/0154973 A1 | 7/2006 | Sheppeck et al. | |
| 2006/0154975 A1 | 7/2006 | Yang et al. | |

FOREIGN PATENT DOCUMENTS

| | | |
|---|---|---|
| CS | 198 678 | 11/1982 |
| DE | 197 42 014 | 3/1999 |
| EP | 0 405 436 | 11/1995 |
| WO | WO93/16982 | 9/1993 |
| WO | WO94/00421 | 1/1994 |
| WO | WO95/05359 | 2/1995 |
| WO | WO95/15947 | 6/1995 |
| WO | WO99/15493 | 4/1999 |
| WO | WO 02/051851 | 7/2002 |
| WO | WO 03/062241 | 7/2003 |
| WO | WO 03/101932 | 12/2003 |
| WO | WO 03/104195 | 12/2003 |
| WO | WO 2004/000869 | 12/2003 |
| WO | WO 2004/005229 | 1/2004 |
| WO | WO 2004/009017 | 1/2004 |
| ZA | 681802 | 3/1968 |

OTHER PUBLICATIONS

Alibert, S. et al., "Synthesis and Effects on Chloroquine Susceptibility in *Plasmodium falciparum* of a Series of New Dihydroanthracene Derivatives", Journal of Medicinal Chemistry, vol. 45, No. 15, pp. 3195-3209 (2002).

Compounds (by Registry Number) with no references in the Chemical Abstracts file: 500280-08-0, 496959-82-1, 332907-97-8, 331751-07-6, 331427-65-7, 312317-98-9, 312315-55-2, 311331-77-8.

(Continued)

*Primary Examiner*—Charanjit S. Aulakh
(74) *Attorney, Agent, or Firm*—Laurelee A. Duncan

(57) ABSTRACT

Novel non-steroidal compounds are provided which are useful in treating diseases associated with modulation of the glucocorticoid receptor, AP-1, and/or NF-κB activity including obesity, diabetes, inflammatory and immune diseases, and have the structure of formula (I)

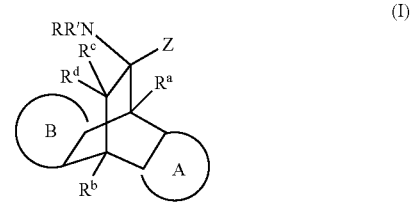

(I)

its stereoisomers thereof, or a solvate thereof, or a prodrug thereof, or a pharmaceutically acceptable salt thereof, where Z is $CONR^1R^2$ or $CH^2NR^1R^2$ and where R, R', $R^a$, $R^b$, $R^c$, $R^d$, Z, A and B are defined herein. Also provided are pharmaceutical compositions and methods of treating obesity, diabetes and inflammatory or immune associated diseases comprising said compounds.

13 Claims, No Drawings

OTHER PUBLICATIONS

El-Zanfally, S. et al., "Reactions of Aminopyridines with some Inner Anhydrides", Egypt J. Pharm. Sci., vol. 17, No. 3, pp. 53-62 (1976).

Kotha, S. et al., "Synthesis of highly constrained unusual α-amino acid derivative by the Diels-Alder approach", Indian Journal of Chemistry, vol. 41B, pp. 2330-2332 (2002).

Pradines, B. et al., "In Vitro Increase in Chloroquine Accumulation Induced by Dihydroethano- Ethenoanthracene Derivatives in *Plasmodium falciparum*-Parasitized Erythrocytes", Antimicrobial Agents and Chemotherapy, vol. 46, No. 7, pp. 2061-2068 (2002).

Baldwin, Jr., A.S., "The transcription factor NF-κB and human disease", The Journal of Clinical Investigation, vol. 107, No. 1, pp. 3-6 (2001).

Bradsher, C.K. et al., "Acridizinium Ion Chemistry. II. The Diels-Alder Reaction", Journal of the American Chemical Society, vol. 80, pp. 933-934 (1958).

Bradsher, C.K. et al., "Addition of Dienophiles to the Acridizinium Ion. III. Evidence for a Two-Step Reaction", The Journal of Organic Chemistry, vol. 34, No. 6, pp. 1700-1702 (1969).

Bradsher, C.K. et al., "Cationic Polar Cycloaddition of Cyclopropenes", J. Org. Chem., vol. 44, No. 8, pp. 1199-1202 (1979).

Bradsher, C.K. et al., "Possible Role of Charge-Transfer Complexes in Cationic Polar Cycloaddition", J. Org. Chem., vol. 43, No. 5, pp. 822-827 (1978).

Bradsher, C.K. et al., "Stereoselectivity Due to Electrostatic Repulsion in the Polar Cycloaddition of the Acridizinium Ion", J. Het. Chem., vol. 10, pp. 1031-1033 (1973).

Bradsher, C.K. et al., "Steric Effects in Some Cycloaddition Reactions", Journal of the American Chemical Society, vol. 99, No. 8, pp. 2588-2591 (1977).

Bradsher, C.K. et al., "The Nature of the Addition of Dienophiles to the Acridizinium Ion", The Journal of Organic Chemistry, vol. 33, No. 2, pp. 519-523 (1968).

Burke, J.R., "Targeting IκB kinase for the treatment of inflammatory and other disorders", Current Opinion in Drug Discovery & Development, vol. 6, No. 5, pp. 720-728 (2003).

Burnham, W.S. et al., "6,11-Dihydroacridizinium Derivatives Having a 6,11-Etheno Bridge", J. Org. Chem., vol. 37, No. 3, pp. 355-358 (1972).

Caldenhoven, E. et al., "Negative Cross-Talk between RelA and the Glucocorticoid Receptor: A Possible Mechanism for the Antiinflammatory Action of Glucocorticoids", Molecular Endocrinology, vol. 9, No. 4, pp. 401-412 (1995).

Chakravarti, D. et al., "Role of CBP/P300 in nuclear receptor signalling", Nature, vol. 383, pp. 99-103 (1996).

Diamond, M.I. et al., "Transcription Factor Interactions: Selectors of Positive or Negative Regulation from a Single DNA Element", Science, vol. 249, pp. 1266-1272 (1990).

Fields, D.L., "A Novel Synthesis of 2-Naphthols, Phenanthrols, Anthracenes, and Other Polycyclic Aromatic Products", J. Org. Chem., vol. 36, No. 20, pp. 3002-3005 (1971).

Fields, D.L. et al., "Azonia Polycyclic Quinones, o-Diazo-Oxides and Related Products", J. Het. Chem., vol. 7, pp. 91-97 (1970).

Fields, D.L. et al., "Cleavage Reactions of Bicyclic Ketones Derived from Azoniaanthracene-Ketene Acetal Adducts", J. Org. Chem., vol. 35, No. 6, pp. 1870-1875 (1970).

Fields, D.L. et al., "Diels-Alder Reactions Involving Azonia Polycyclic Aromatic Compounds and Nucleophilic Dienophiles", J. Org. Chem., vol. 33, No. 1, pp. 390-395 (1968).

Fields, D.L. et al., "Overcrowded Molecules. I. Substituted 8-*tert*-Butyl-1-(2-pyridyl)naphthalenes, Including a Thermodynamically Stable Ketonic Tautomer", J. Org. Chem., vol. 36, No. 20, pp. 2986-2990 (1971).

Fields, D.L. et al., "Overcrowded Molecules. II. 4,5-Bis(2-pyridyl)phenanthrene-3,6-diols", J. Org. Chem., vol. 36, No. 20, pp. 2991-2995 (1971).

Fields, D.L. et al., "Overcrowded Molecules. III. 13, 14-Bis(2-pyridyl)pentaphene and Related Compounds", J. Org. Chem., vol. 36, No. 20, pp. 2995-3001 (1971).

Firestein, G.S. et al., "Signal Transduction and Transcription Factors in Rheumatic Disease", Arthritis & Rheumatism, vol. 42, No. 4, pp. 609-621 (1999).

Hart, H. et al., "1,4,5,8,9-pentamethylanthracene, Synthesis and Protonation", Tetrahedron Letters, vol. 16, No. 52, pp. 4639-4642 (1975).

Jackson, R.W. et al., "Benzobicyclooctanes as Novel Inhibitors of TNF-α Signaling", Bioorganic & Medicinal Chemistry Letters, vol. 12, pp. 1093-1097 (2002).

Jonat, C. et al., "Antitumor Promotion and Antiinflammation: Down-Modulation of AP-1 (Fos/Jun) Activity by Glucocorticoid Hormone", Cell, vol. 62, pp. 1189-1204 (1990).

Kamei, Y. et al., "A CBP Integrator Complex Mediates Transcriptional Activation and AP-1 Inhibition by Nuclear Receptors", Cell, vol. 85, pp. 403-414 (1996).

Manning, A.M. et al., "Targeting JNK for Therapeutic Benefit: From Junk to Gold", Nature Reviews Drug Discovery, vol. 2, pp. 554-565 (2003).

Miesfeld, R. et al., "Characerization of a steroid hormone receptor gene and mRNA in wild-type and mutant cells", Nature, vol. 312, pp. 779-781 (1984).

Parham, M.E. et al., "The Cycloaddition of the Acridizinium Ion with Norbornene Derivatives", J. Org. Chem., vol. 37, No. 3, pp. 358-362 (1972).

Peltz, G., "Transcription factors in immune-mediated disease", Current Opinion in Biotechnology, vol. 8, pp. 467-473 (1997).

Prostakov, N.S. et al., "Hydrogenation and halogenation of 6-phenyl-5-azabenzo[f]fluoranthene and reduction of its adducts with acrylonitrile", Khimiya Geterotsiklicheskikh Soedinenii, vol. 2, pp. 233-235 (1982), abstract only.

Reichardt, H.M. et al., "DNA Binding of the Glucocorticoid Receptor Is Not Essential for Survival", Cell, vol. 93, pp. 531-541 (1998).

Reichardt, H.M. et al., "Repression of inflammatory responses in the absence of DNA binding by the glucocorticoid receptor", The EMBO Journal, vol. 20, No. 24, pp. 7168-7173 (2001).

Weinberger, C. et al., "Domain structure of human glucocorticoid receptor and its relationship to the v-*erb*-A oncogene product", Nature, vol. 318, pp. 670-672 (1985).

Weinberger, C. et al., "Identification of Human Glucocorticoid Receptor Complementary DNA Clones by Epitope Selection", Science, vol. 228, pp. 740-742 (1985).

Westerman, I.J. et al., "Rates of Addition of Styrene to 9-Substituted Acridizinium Ions", J. Org. Chem., vol. 36, No. 7, pp. 969-970 (1971).

Westerman, I.J. et al., "Regiochemistry of Polar Cycloaddition. Validity of the Electrophilic Addition Model", J. Org. Chem., vol. 43, No. 15, pp. 3002-3006 (1978).

Westerman, I.J. et al., "Stereochemistry of Cationic Polar Cycloaddition", J. Org. Chem., vol. 44, No. 5, pp. 727-733 (1979).

Yang-Yen, H.-F. et al., "Transcriptional Interference between c-Jun and the Glucocorticoid Receptor: Mutant Inhibition of DNA Binding Due to Direct Protein-Protein Interaction", Cell, vol. 62, pp. 1205-1215 (1990).

U.S. Appl. No. 11/330,749, filed Jan. 12, 2006, Bristol-Myers Squibb Co.

MODULATORS OF GLUCOCORTICOID RECEPTOR, AP-1, AND/OR NF-κβ ACTIVITY AND USE THEREOF

This application claims priority from U.S. Provisional Application No. 60/537,470, filed Jan. 16, 2004, incorporated herein by reference in its entirety.

FIELD OF THE INVENTION

The present invention relates to new non-steroidal compounds which are which are particularly effective modulators of the glucocorticoid receptor, AP-1, and/or NF-κB activity and thus are useful in treating diseases such as obesity, diabetes and inflammatory or immune associated diseases, and to a method for using such compounds to treat these and related diseases.

BACKGROUND OF THE INVENTION

The transcription factors NF-κB and AP-1 are involved in regulating the expression of a number of genes involved in mediating inflammatory and immune responses. NF-κB regulates the transcription of genes including TNF-α, IL-1, IL-2, IL-6, adhesion molecules (such as E-selectin) and chemokines (such as Rantes), among others. AP-1 regulates the production of the cytokines TNF-α, IL-1, IL-2, as well as, matrix metalloproteases. Drug therapies targeting TNF-α, a gene whose expression is regulated by both NF-κB and AP-1, have been shown to be highly efficacious in several inflammatory human diseases including rheumatoid arthritis and Crohn's disease. Accordingly, NF-κB and AP-1 play key roles in the initiation and perpetuation of inflammatory and immunological disorders. See Baldwin, A S, *Journal of Clin. Investigation*, 107, 3 (2001); Firestein, G. S., and Manning, A. M., *Arthritis and Rheumatism*, 42, 609 (1999); and Peltz, G., *Curr. Opin, in Biotech.* 8, 467 (1997).

There are many signaling molecules (kinases and phosphatases) upstream of AP-1 and NF-κB which are potential therapeutic drug targets. The kinase JNK plays an essential role in regulating the phosphorylation and subsequent activation of c-jun, one of the subunits which constitute the AP-1 complex (fos/c-jun). Compounds which inhibit JNK have been shown to be efficacious in animal models of inflammatory disease. See Manning A M and Davis R J, *Nature Rev. Drug Disc.*, V. 2, 554 (2003). A kinase critical to the activation of NF-κB is the IκB kinase (IKK). This kinase plays a key role in the phosphorylation of IκB. Once IκB is phosphorylated it undergoes degradation leading to the release of NF-κB which can translocate into the nucleus and activate the transcription of the genes described above. An inhibitor of IKK, BMS-345541, has been shown to be efficacious in animal models of inflammatory disease. See Burke J R., *Curr Opin Drug Discov Devel.*, September;6(5), 720-8, (2003).

In addition to inhibiting signaling cascades involved in the activation of NF-κB and AP-1, the glucocorticoid receptor has been shown to inhibit the activity of NF-κB and AP-1 via direct physical interactions. The glucocorticoid receptor (GR) is a member of the nuclear hormone receptor family of transcription factors, and a member of the steroid hormone family of transcription factors. Affinity labeling of the glucocorticoid receptor protein allowed the production of antibodies against the receptor which facilitated cloning the glucocorticoid receptors. For results in humans see Weinberger, et al., *Science* 228, 640-742, (1985); Weinberger, et al., *Nature*, 318, 670-672 (1986) and for results in rats see Miesfeld, R., *Nature*, 312, 779-781, (1985).

Glucocorticoids which interact with GR have been used for over 50 years to treat inflammatory diseases. It has been clearly shown that glucocorticoids exert their anti-inflammatory activity via the inhibition by GR of the transcription factors NF-κB and AP-1. This inhibition is termed transrepression. It has been shown that the primary mechanism for inhibition of these transcription factors by GR is via a direct physical interaction. This interaction alters the transcription factor complex and inhibits the ability of NF-κB and AP-1 to stimulate transcription. See Jonat, C., et al., *Cell*, 62, 1189 (1990); Yang-Yen, H. F., et al,. *Cell*, 62, 1205 (1990); Diamond, M. I. et al., *Science* 249, 1266 (1990); and Caldenhoven, E. et al., *Mol. Endocrinol.*, 9, 401 (1995). Other mechanisms such as sequestration of co-activators by GR have also been proposed. See Kamer Y, et al., *Cell*, 85, 463 (1996); and Chakravarti, D. et al., *Nature*, 383, 99 (1996).

In addition to causing transrepression, the interaction of a glucocorticoid with GR can cause GR to induce transcription of certain genes. This induction of transcription is termed transactivation. Transactivation requires dimerization of GR and binding to a glucocorticoid response element (GRE).

Recent studies using a transgenic GR dimerization defective mouse which cannot bind DNA have shown that the transactivation (DNA binding) activities of GR could be separated from the transrepressive (non-DNA binding) effect of GR. These studies also indicate that many of the side effects of glucocorticoid therapy are due to the ability of GR to induce transcription of various genes involved in metabolism, whereas, transrepression, which does not require DNA binding leads to suppression of inflammation. See Tuckermann, J. et al., *Cell*, 93, 531 (1998) and Reichardt, H M, *EMBO J.,* 20, 7168 (2001).

PCT application WO 2004/009017 published Jan. 29, 2004, assigned to Applicant and incorporated herein by reference in its entirety, describes substituted bicyclooctanes useful in treating diseases such as obesity, diabetes and inflammatory or immune associated diseases.

Compounds that modulate AP-1 and NF-κB activity would be in the treatment of inflammatory and immune diseases and disorders such as osteoarthritis, rheumatoid arthritis, multiple sclerosis, asthma, inflammatory bowel disease, transplant rejection and graft vs. host disease.

Also, with respect to the glucocorticoid receptor pathway, it is known that glucocorticoids are potent anti-inflammatory agents, however their systemic use is limited by side effects. Compounds that retain the anti-inflammatory efficacy of glucocorticoids while minimizing the side effects such as diabetes, osteoporosis and glaucoma would be of great benefit to a very large number of patients with inflammatory diseases.

Additionally concerning GR, the art is in need of compounds that antagonize transactivation. Such compounds may be useful in treating metabolic diseases associated with increased levels of glucocorticoid, such as diabetes, osteoporosis and glaucoma.

Additionally concerning GR, the art is in need of compounds that cause transactivation. Such compounds may be useful in treating metabolic diseases associated with a deficiency in glucocorticoid. Such diseases include Addison's disease.

DESCRIPTION OF THE INVENTION

The present invention relates to new non-steroidal compounds which are which are particularly effective modulators of the glucocorticoid receptor, AP-1, and/or NF-κB activity and thus are useful in treating diseases such as obesity, diabetes and inflammatory or immune associated diseases, and to a method for using such compounds to treat these and related diseases.

In accordance with the present invention, compounds are provided having the structure of formula (I)

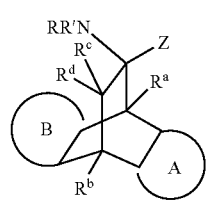

its stereoisomers thereof, or a solvate thereof, or a pharmaceutically acceptable salt thereof, wherein R is hydrogen, alkyl, alkenyl, alkynyl, cycloalkyl, cycloalkylalkyl, aryl, heteroaryl, heteroarylalkyl, cycloheteroalkyl, cycloalkenyl, monoalkylaminoalkyl, dialkylaminoalkyl, cycloheteroalkylalkyl, hydroxyaryl, aryloxyalkyl, alkoxyalkyl and hydroxyalkyl, $S(O)_tR_3$, or $C(O)_tR_3$ wherein $R^3$ is selected from hydrogen, alkyl, alkenyl, alkynyl, alkoxy, cycloalkyl, cycloalkylalkyl, aryl, heteroaryl, heteroarylalkyl, cycloheteroalkyl, cycloalkenyl, monoalkylaminoalkyl, dialkylaminoalkyl, cycloheteroalkylalkyl, hydroxyaryl, aryloxyalkyl, alkoxyalkyl and hydroxyalkyl;

R' is selected from hydrogen, alkyl, alkenyl, alkynyl, alkoxy, cycloalkyl, cycloalkylalkyl, aryl, heteroaryl, heteroarylalkyl, cycloheteroalkyl, cycloalkenyl, monoalkylaminoalkyl, dialkylaminoalkyl, cycloheteroalkylalkyl, hydroxyaryl, aryloxyalkyl, alkoxyalkyl and hydroxyalkyl;

$R^a$ and $R^b$ are independently selected from hydrogen, halogen, hydroxy, alkyl, alkenyl, alkynyl, alkoxy, aryl, aryloxy, heteroaryl, cycloheteroalkyl, heteroarylalkyl, cycloheteroalkylalkyl, cyano, heteroarylaminocarboyl, cycloheteroalkylcarbonyl, cyanoalkyl, alkylaminoalkyl, hydroxyalkyl, hydroxyaryl, aryloxyalkyl, alkoxyalkyl, nitro, $NR^eR^f$, CHO, $CO_2$alkyl, $CONR^eR^f$, $CH_2NR^eR^f$, $CO_2H$, $CH_2OH$, $CH_2NR^eR^f$, $NHCOR^g$, $NHCONR^eR^f$ and $NHSO_2R^g$;

$R^c$ and $R^d$ are independently selected from hydrogen, alkyl, alkenyl, alkynyl, alkoxy, $NR^eR^f$, aryl, hydroxy, aryloxy, heteroaryl, cycloheteroalkyl, heteroarylalkyl, cycloheteroalkylalkyl, hydroxyaryl, and aryloxyalkyl;

$R^e$ and $R^f$ at each occurrence are the same or different and are independently selected from hydrogen, aryl, alkyl, alkenyl, alkynyl, alkoxy, amino, substituted amino, alkoxyalkyl, alkylaminoalkyl, dialkylaminoalkyl, heteroaryl, cycloheteroalkyl, heteroarylalkyl, cycloheteroalkylalkyl, cycloalkyl, and cycloalkylalkyl, provided $R^e$ and $R^f$ are not both alkoxy or amino;

or $R^e$ and $R^f$ at each occurrence can be taken together with the nitrogen to which they are attached to form a 5-, 6- or 7-membered heteroaryl or cycloheteroalkyl ring which contains 1, 2 or 3 hetero atoms which can be N, O or S;

$R^g$ at each occurrence is selected from hydrogen, aryl, alkyl, alkenyl, alkynyl, alkoxy, amino, substituted amino, alkoxyalkyl, alkylaminoalkyl, dialkylaminoalkyl, heteroaryl, cycloheteroalkyl, heteroarylalkyl, cycloheteroalkylalkyl, cycloalkyl and cycloalkylalkyl;

Z is $S(O)_tNR^1R^2$, $C(O)NR^1R^2$ or $CH_2NR^1R^2$ wherein $R^1$ and $R^2$ are the same or different and are independently selected from hydrogen, alkyl, alkenyl, alkynyl, alkoxy, cycloalkyl, cycloalkylalkyl, aryl, heteroaryl, heteroarylalkyl, cycloheteroalkyl, cycloalkenyl, monoalkylaminoalkyl, dialkylaminoalkyl, cycloheteroalkylalkyl, hydroxyaryl, aryloxyalkyl, alkoxyalkyl or hydroxyalkyl;

t is 1 or 2;

each occurrence of t, $R^e$, $R^f$, and $R^g$ are chosen independently;

the A ring represents a saturated, partially saturated or unsaturated 6-membered carbocyclic or heterocyclic ring; and the B ring represents a saturated, partially saturated or unsaturated 6-membered carbocyclic or heterocyclic ring.

Preferred compounds within the scope of formula (I), above, are those in which R' is hydrogen and the A ring has the structure

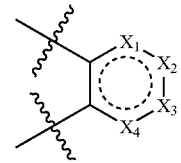

and the B ring has the structure

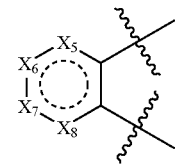

$X_1$, $X_2$, $X_3$ and $X_4$, are the same or different and are independently selected from CH, $CH_2$, $CHR^4$, $CR^5$, $R^6$, N, NH, $NR^7$, O or S, and $X_5$, $X_6$, $X_7$ and $X_8$ are the same or different and are independently selected from CH, $CH_2$, $CHR^8$, $CR^9R^{10}$, N, NH, $NR^{11}$, O or S;

$R^4$, $R^5$, $R^6$, $R^8$, $R^9$, $R^{10}$ and $R^{12}$ are the same or different and are independently selected from hydrogen, halo, alkyl, aryl, cycloalkyl, heteroaryl, cycloheteroalkyl, hydroxy, alkoxy, aryloxy, cyano, nitro, $NR^eR^f$, CHO, —$CO_2$alkyl, hydroxyaryl, aryloxyalkyl, $OCONR^eR^f$, $OCOR^e$, $OCOOR^eR^f$, —OCO-aryl, —OCO-heteroaryl, $CONR^eR^f$, $CO_2H$, $OCSOR^eR^f$, $CSNR^eR^f$ $NHCOR^i$, $NHCONR^eR^f$, $NHCSNR^eR^f$, $NHSO_pR^i$, —$SO_2NR^eR^f$, $NR^eSO_2NR^eR^f$, and $NR^eSO_pR^i$;

$R^7$ and $R^{11}$ are independently selected from hydrogen, aryl, alkyl, alkenyl, alkynyl, alkoxy, amino, substituted amino, alkoxyalkyl, $CO_2$alkyl, C(O)alkyl alkylaminoalkyl, dialkylaminoalkyl, heteroaryl, cycloheteroalkyl, heteroarylalkyl, cycloheteroalkylalkyl, cycloalkyl, and cycloalkylalkyl;

each occurrence of $R^4$, $R^5$, $R^6$, $R^7$, $R^8$, $R^9$, $R^{11}$ and $R^{12}$ is chosen independently; and each of said A ring and said B ring contains at most two nitrogen ring atoms, at most two oxygen ring atom and at most one sulfur ring atom.

Also preferred are compounds within the scope of formula (I), above, having a structure of the formulae (IIA), (IIB) or (IIC):

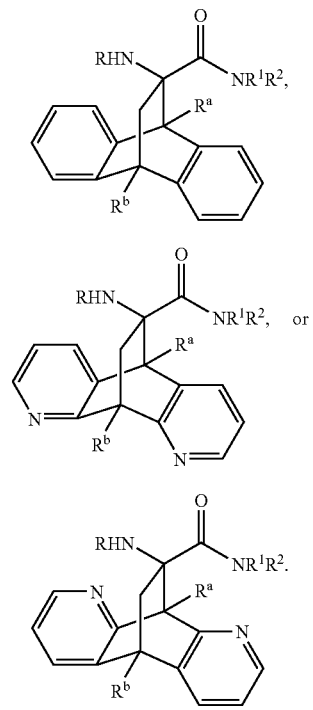

Whether or not specifically listed, all preferred compounds described herein include prodrugs thereof, as well as stereoisomers thereof, a solvate thereof, or pharmaceutically acceptable salts thereof. Other especially preferred compounds include those described in paragraphs 1-7 (below).

1. Preferred compounds within the scope of formulae IIA, IIB and IIC (above) are those in which one of $R^1$ and $R^2$ is heteroaryl.

2. Preferred compounds within the scope of numbered paragraph 1 are those in which one of $R^1$ and $R^2$ is selected from

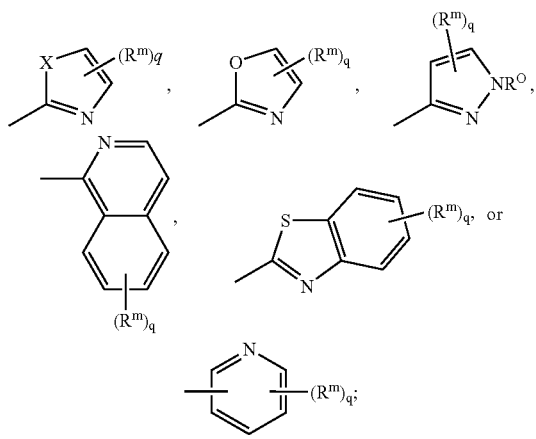

where $R^m$ is selected from H, halo, nitro, cyano, hydroxy, alkoxy; alkyl, aryl or heteroaryl, X is S or NH; q is 1 or 2; and $R^O$ is H or alkyl.

4. Other preferred compounds are those within the scope of paragraph 3, having a structure of the following formulae (IIIA), (IIIB), (IIIC), or (IIID):

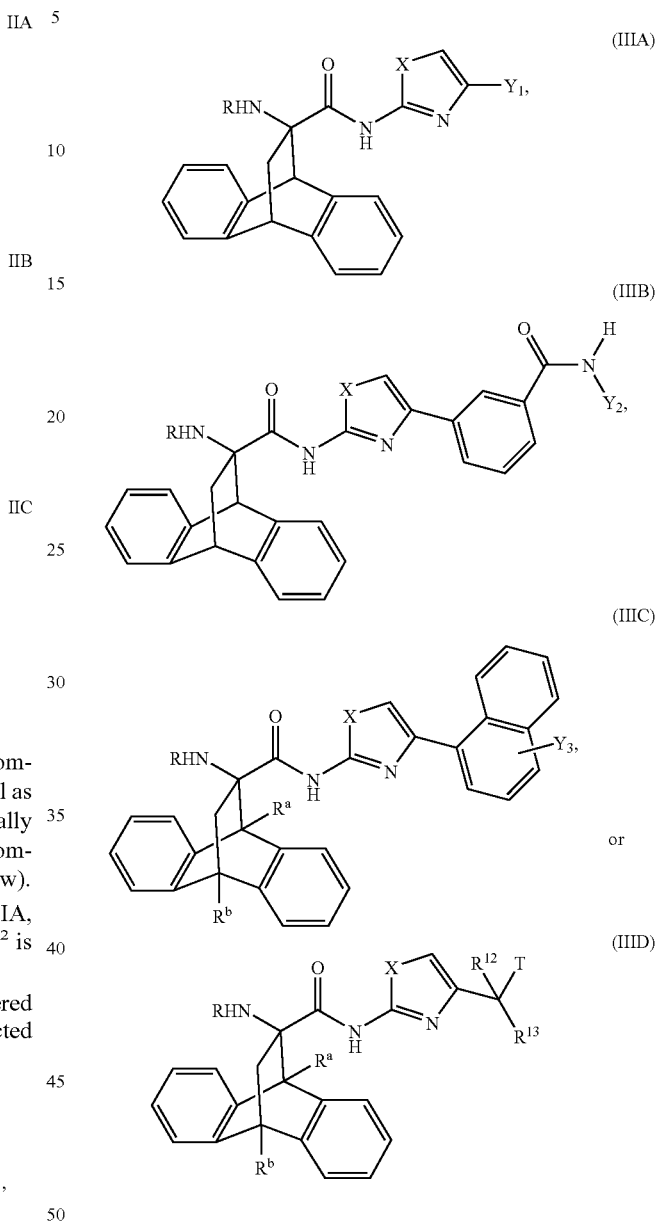

wherein:

$R^a$ is alkyl, halogen, hydrogen alkoxycarbonyl ($CO_2$ alkyl), nitro, or cyano;

$R^b$ is hydrogen, alkyl, halogen, $CO_2$alkyl, nitro, cyano, formyl, cycloheteroalkylcarbonyl, alkylaminoalkyl or amino, X is O, S, or NH;

$Y_1$ is hydrogen, halogen, nitro, cyano, hydroxy, alkoxy, or alkyl substituted with hydrogen, aryl or heteroaryl;

$Y_2$ is phenyl substituted by 1 to 3 groups selected from hydrogen, halogen, nitro, cyano, hydroxy, alkoxy; alkyl, aryl and heteroaryl;

$Y_3$ is hydrogen, halogen, nitro, cyano, hydroxy, alkoxy; or alkyl;

T is a cycloalkyl, cycloalkenyl, heterocycloalkyl, aryl, or heteroaryl ring, each ring substituted by 0-1 $R^{14}$ and 0-4 $R^{15}$;

$R^{12}$ and $R^{13}$ are independently at each occurrence hydrogen, halogen, hydroxy, alkyl, alkenyl, alkynyl, alkoxy, cyano, nitro, $NR^eR^f$, or CHO;

or $R^{12}$ and $R^{13}$ combine to form =O or a double bond, wherein the double bond is substituted by hydrogen, aryl, alkyl, alkenyl, alkynyl, alkoxy, amino, substituted amino, alkoxyalkyl, alkylaminoalkyl, dialkylaminoalkyl, heteroaryl, cycloheteroalkyl, heteroarylalkyl, cycloheteroalkylalkyl, cycloalkyl, or cycloalkylalkyl;

$R^{14}$ and $R^{15}$ are, independently at each occurrence, hydrogen, halogen, hydroxy, alkyl, alkenyl, alkynyl, alkoxy, aryl, aryloxy, heteroaryl, cycloheteroalkyl, heteroarylalkyl, cycloheteroalkylalkyl, cyano, heteroarylaminocarboyl, cycloheteroalkylcarbonyl, cyanoalkyl, alkylaminoalkyl, hydroxyalkyl, hydroxyaryl, aryloxyalkyl, nitro, oxo, $NR^eR^f$, CHO, $CO_2$ alkyl, hydroxyaryl, aryloxyalkyl, $CONR^eR^f$, $CH_2NR^eR^f$, $CO_2H$, $CH_2OH$, $CH_2NHC(O)R^eR^f$, $NHCOR^g$, $NHCONR^eR^f$, $NHSO_pR^g$, $-SO_2NR^eR^f$, $NR^eSO_2NR^eR^f$, or $NR^eSO_pR^g$;

or $R^{14}$ and $R^{15}$ located on adjacent atoms can be taken together to form an optionally substituted cycloalkyl, aryl, heteroaryl, or cycloheteroalkyl ring.

5. Other preferred compoundsare those within the scope of numbered paragraph 4, above have a structure of the formula (IV):

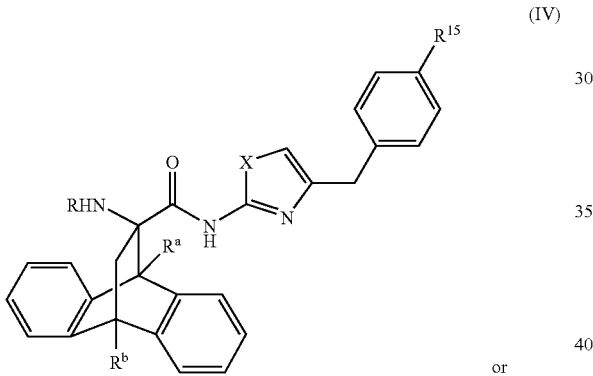

(IV)

or its stereoisomers thereof, or a solvate thereof, or a pharmaceutically acceptable salt thereof, wherein:

X is S, or NH;

R is hydrogen or $C(O)C_{1-4}$alkyl; and $R^{15}$ is $C_{1-4}$alkoxy; halogen, pyrimidine, isoxazole, pyrazole, or pyridine, where the $C_{1-4}$alkoxy; pyrimidine, isoxazole, pyrazole, or pyridine, groups are substituted by hydrogen, morpholinyl, or $C_{1-4}$alkyl.

6. Other preferred compoundsare those within the scope of numbered paragraph 4 have a structure of the formula (V):

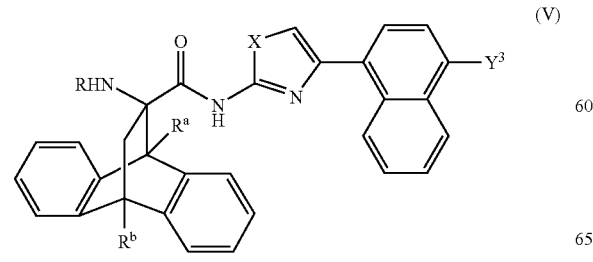

(V)

its stereoisomers thereof, or a solvate thereof, or a pharmaceutically acceptable salt thereof, wherein:

X is S, or NH;

R is hydrogen or $C(O)C_{1-4}$alkyl; and $Y^3$ is hydrogen, $C_{1-4}$alkyl, or halogen.

7. A compound having a structure selected from the following:

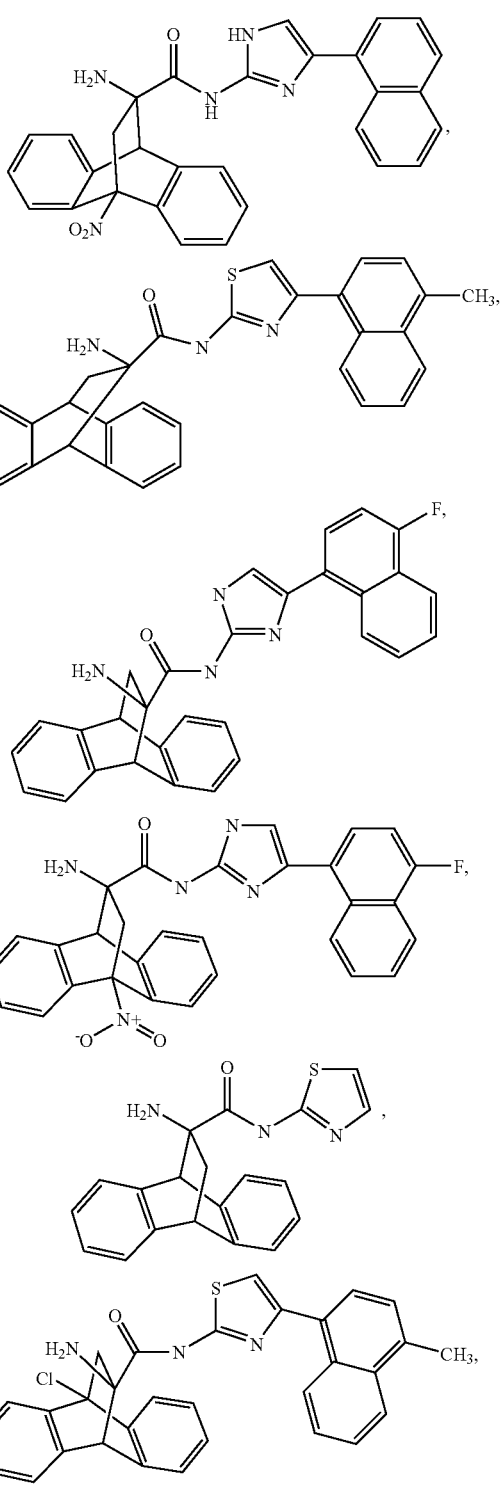

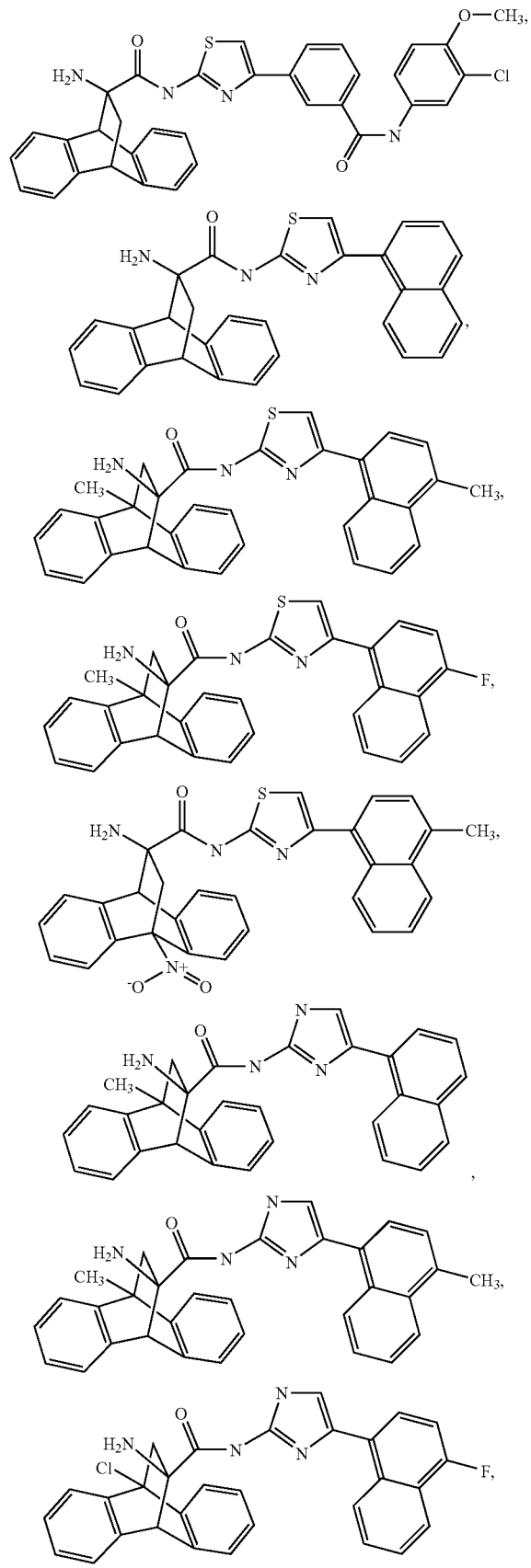
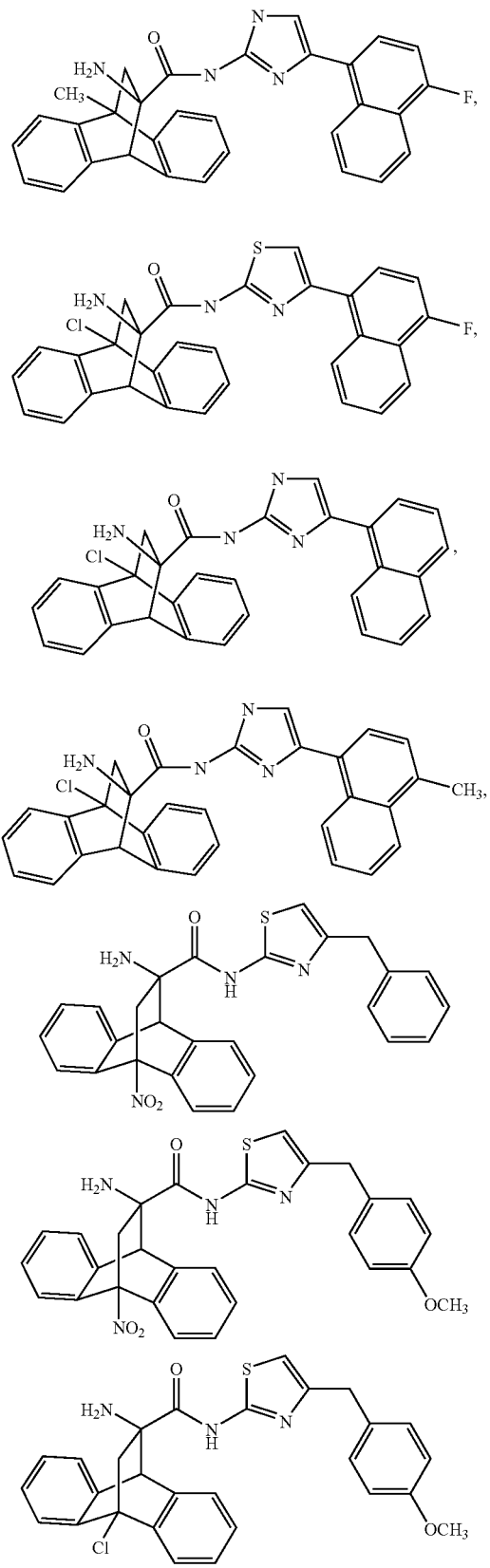

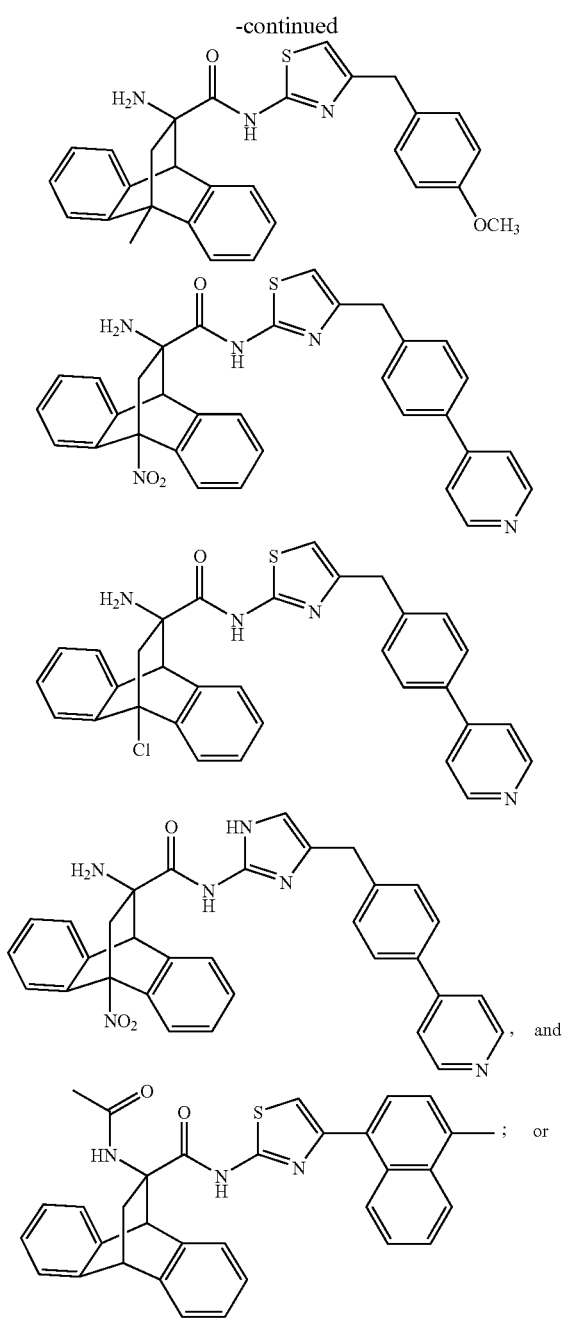

(ii) a stereoisomer of (i) thereof, a solvate of (i) thereof, or pharmaceutically acceptable salt of (i), thereof.

In another embodiment of the present invention, there is provided pharmaceutical compositions useful in treating endocrine disorders, rheumatic disorders, collagen diseases, dermatologic disease, allergic disease, ophthalmic disease, respiratory disease, hematologic disease, gastrointestinal disease, inflammatory disease, autoimmune disease, diabetes, obesity, and neoplastic disease, as well as other uses as described herein, which includes a therapeutically effective amount (depending upon use) of a compound of formula (I) of the invention and a pharmaceutically acceptable carrier.

In still another embodiment, the present invention provides a method of treating endocrine disorders, rheumatic disorders, collagen diseases, dermatologic disease, allergic disease, ophthalmic disease, respiratory disease, hematologic disease, gastrointestinal disease, inflammatory disease, autoimmune disease, diabetes, obesity, and neoplastic disease, that is a disease associated with the expression product of a gene whose transcription is stimulated or repressed by glucocorticoid receptors, or a disease associated with AP-1- and/or NFκB (particularly AP-1-)-induced transcription, or a disease associated with AP-1 and/or NFκB-(particularly AP-1-) dependent gene expression, wherein the disease is associated with the expression of a gene under the regulatory control of AP-1 and/or NF-κB (particularly AP-1), including inflammatory and immune diseases and disorders as described hereinafter, which includes the step of administering a therapeutically effective amount of a compound of formula (I) of the invention to a patient.

Another embodiment of the present invention involves a method for treating a disease or disorder associated with the expression product of a gene whose transcription is stimulated or repressed by glucocorticoid receptors, or a method of treating a disease or disorder associated with AP-1- and/or NF-κB-(particularly AP-1-) induced transcription, or a method for treating a disease or disorder associated with AP-1 and/or NF-κB (particularly AP-1) dependent gene expression, wherein the disease is associated with the expression of a gene under the regulatory control of AP-1 and/or NF-κβ (particularly AP-1), such as inflammatory and immune disorders, cancer and tumor disorders, such as solid tumors, lymphomas and leukemia, and fungal infections such as mycosis fungoides.

The term "disease associated with GR transactivation," as used herein, refers to a disease associated with the transcription product of a gene whose transcription is transactivated by a GR. Such diseases include, but are not limited to: osteoporosis, diabetes, glaucoma, muscle loss, facial swelling, personality changes, hypertension, obesity, depression, and AIDS, the condition of wound healing, primary or secondary andrenocortical insufficiency, and Addison's disease.

The term "treat", "treating", or "treatment," in all grammatical forms, as used herein refers to the prevention, reduction, or amelioration, partial or complete alleviation, or cure of a disease, disorder, or condition, wherein prevention indicates treatment of a person at risk for developing such a disease, disorder or condition.

The terms "glucocorticoid receptor" and "GR," as used herein, refer either to a member of the nuclear hormone receptor ("NHR") family of transcription factors which bind glucocorticoids and either stimulate or repress transcription, or to GR-beta. These terms, as used herein, refer to glucocorticoid receptor from any source, including but not limited to: human glucocorticoid receptor as disclosed in Weinberger, et al. *Science* 228, p640-742 (1985), and in Weinberger, et al. *Nature,* 318, p670-672 (1986); rat glucocorticoid receptor as disclosed in Miesfeld, R. *Nature,* 312, p779-781 (1985); mouse glucocortoid receptor as disclosed in Danielson, M. et al. *EMBO J.,* 5, 2513; sheep glucocorticoid receptor as disclosed in Yang, K., et al. *J. Mol. Endocrinol.* 8, p173-180 (1992); marmoset glucocortoid receptor as disclosed in Brandon, D. D., et al, *J. Mol. Endocrinol.* 7, p89-96 (1991); and human GR-beta as disclosed in Hollenberg, S M. et al. *Nature,* 318, p635, 1985, Bamberger, C. M. et al. *J. Clin Invest.* 95, p2435 (1995).

The term, "disease or disorder associated with AP-1 and/or NF-κB" as used herein, refers to a disease associated with the expression product of a gene under the regulatory control of AP-1 and/or NF-κB. Such diseases include, but are not limited to: inflammatory and immune diseases and disorders; cancer and tumor disorders, such as solid tumors, lymphomas and leukemia; and fungal infections such as mycosis fungoides.

The term "inflammatory or immune associated diseases or disorders" is used herein to encompass any condition, disease, or disorder that has an inflammatory or immune component, including, but not limited to, each of the following conditions: transplant rejection (e.g., kidney, liver, heart, lung, pancreas (e.g., islet cells), bone marrow, cornea, small bowel, skin allografts, skin homografts (such as employed in burn treatment), heart valve xenografts, serum sickness, and graft vs. host disease, autoimmune diseases, such as rheumatoid arthritis, psoriatic arthritis, multiple sclerosis, Type I and Type II diabetes, juvenile diabetes, obesity, asthma, inflammatory bowel disease (such as Crohn's disease and ulcerative colitis), pyoderma gangrenum, lupus (systemic lupus erythematosis), myasthenia gravis, psoriasis, dermatitis, dermatomyositis; eczema, seborrhoea, pulmonary inflammation, eye uveitis, hepatitis, Grave's disease, Hashimoto's thyroiditis, autoimmune thyroiditis, Behcet's or Sjorgen's syndrome (dry eyes/mouth), pernicious or immunohaemolytic anaemia, atherosclerosis, Addison's disease (autoimmune disease of the adrenal glands), idiopathic adrenal insufficiency, autoimmune polyglandular disease (also known as autoimmune polyglandular syndrome), glomerulonephritis, scleroderma, morphea, lichen planus, vitelligo (depigmentation of the skin), alopecia areata, autoimmune alopecia, autoimmune hypopituatarism, Guillain-Barre syndrome, and alveolitis; T-cell mediated hypersensitivity diseases, including contact hypersensitivity, delayed-type hypersensitivity, contact dermatitis (including that due to poison ivy), uticaria, skin allergies, respiratory allergies (hayfever, allergic rhinitis) and gluten-sensitive enteropathy (Celiac disease); inflammatory diseases such as osteoarthritis, acute pancreatitis, chronic pancreatitis, acute respiratory distress syndrome, Sezary's syndrome and vascular diseases which have an inflammatory and or a proliferatory component such as restenosis, stenosis and artherosclerosis. Inflammatory or immune associated diseases or disorders also includes, but is not limited to: endocrine disorders, rheumatic disorders, collagen diseases, dermatologic disease, allergic disease, ophthalmic disease, respiratory disease, hematologic disease, gastrointestinal disease, inflammatory disease, autoimmune disease, congenital adrenal hyperplasia, nonsuppurative thyroiditis, hypercalcemia associated with cancer, juvenile rheumatoid arthritis, Ankylosing spondylitis, acute and subacute bursitis, acute nonspecific tenosynovitis, acute gouty arthritis, post-traumatic osteoarthritis, synovitis of osteoarthritis, epicondylitis, acute rheumatic carditis, pemphigus, bullous dermatitis herpetiformis, severe erythema multiforme, exfoliative dermatitis, seborrheic dermatitis, seasonal or perennial allergic rhinitis, bronchial asthma, contact dermatitis, atopic dermatitis, drug hypersensitivity reactions, allergic conjunctivitis, keratitis, herpes zoster ophthalmicus, iritis and iridocyclitis, chorioretinitis, optic neuritis, symptomatic sarcoidosis, fulminating or disseminated pulmonary tuberculosis chemotherapy, idiopathic thrombocytopenic purpura in adults, secondary thrombocytopenia in adults, acquired (autoimmune) hemolytic anemia, leukemias and lymphomas in adults, acute leukemia of childhood, regional enteritis, autoimmune vasculitis, multiple sclerosis, chronic obstructive pulmonary disease, solid organ transplant rejection, sepsis. Preferred treatments include treatment of transplant rejection, rheumatoid arthritis, psoriatic arthritis, multiple sclerosis, Type 1 diabetes, asthma, inflammatory bowel disease, systemic lupus erythematosis, psoriasis and chronic pulmonary disease.

In addition, in accordance with the present invention a method of treating a disease associated with AP-1-induced and/or NF-κB-induced transcription (particularly AP-1-induced transcription) is provided wherein a compound of formula (I) of the invention is administered to a patient at risk of developing the disease in a therapeutically effective amount to induce NHR transrepression of the AP-1-induced and/or NF-κB-induced transcription (particularly AP-1-induced transcription), thereby treating the disease.

Other therapeutic agents, such as those described hereafter, may be employed with the compounds of the invention in the present methods. In the methods of the present invention, such other therapeutic agent(s) may be administered prior to, simultaneously with or following the administration of the compound(s) of the present invention.

In a particular embodiment, the compounds of the present invention are useful for the treatment of the aforementioned exemplary disorders irrespective of their etiology, for example, for the treatment of transplant rejection, rheumatoid arthritis, inflammatory bowel disease, and viral infections.

Methods of Synthesis

The compounds of the present invention may be synthesized by many methods available to those skilled in the art of organic chemistry. General synthetic schemes, in accordance with the present invention, for preparing compounds of the present invention are described below. These schemes are illustrative and are not meant to limit the possible techniques one skilled in the art may use to prepare the compounds disclosed herein. Different methods to prepare the compounds of the present invention will be evident to those skilled in the art. Additionally, the various steps in the synthesis may be performed in an alternate sequence in order to give the desired compound or compounds. Examples of compounds of the present invention prepared by methods described in the general schemes are given in the preparations and examples section set out hereinafter.

Compounds of Formula (I)

Compounds of formula (I) of the invention are prepared as described in the Schemes and examples below. In the schemes the various groups $X_1$, $X_2$, $X_3$, $X_4$, $X_5$, $X_6$, $X_7$, $X_8$, Z, R, $R^a$, $R^b$, $R^c$, and $R^d$ correspond to those described above.

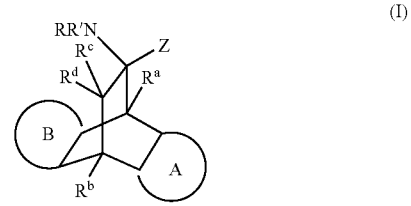

(I)

Scheme A

Compounds of formula (IA) of the invention in which A and B are each fused phenyl or pyridyl rings and Z is —COOH are constructed by the cycloaddition of a compound of formula 1 with an unsaturated compound of formula 2 neat or in an appropriate solvent such as xylenes, toluene, nitrobenzene or benzene, at temperatures ranging from room temperature to 200° C. to form compound 3. It is well known that the cycloaddition may be facilitated by the use of catalysts such as diethylaluminium chloride, titanium tetrachloride or boron trifluoride diethyl etherate. The cycloaddition may also be carried out at higher pressures as when the reactions are performed in sealed vessels. Microwave technology may be applied to the cycloaddition to facilitate the formation of the cycloadduct in solvents such as nitrobenzene, toluene, dichlorobenzene and DMF at temperatures ranging from 100 to 250° C. for 15 to 120 minutes.

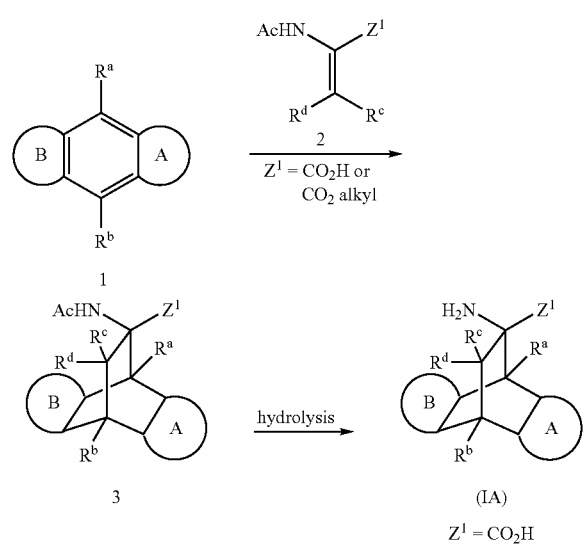

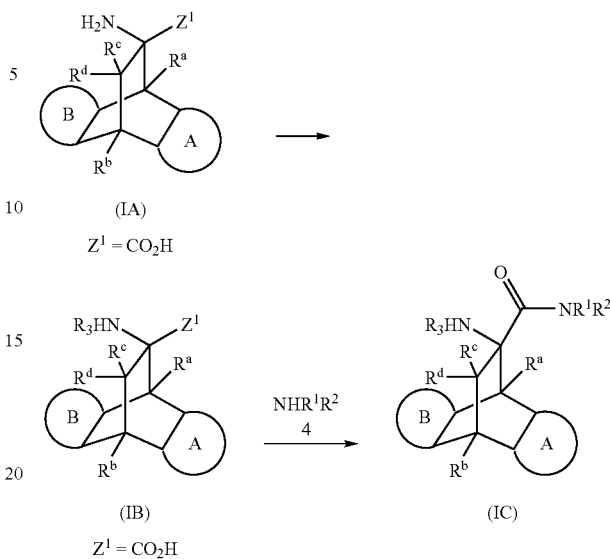

Scheme C

Compounds of formula (ID) of the invention where Z is —CONR$^1$R$^2$ and R$_3$=H, may be prepared from compounds of formula (IC) using one of the many deprotection methods for amines well known to those skilled in the art (such as treatment with TFA in dichloromthane to remove the BOC group from the nitrogen). Additionally, compounds of formula (ID) can be converted to other nitrogen derivatives, such as primary or secondary alkylamine, or amide by various methods well known to those skilled in the art.

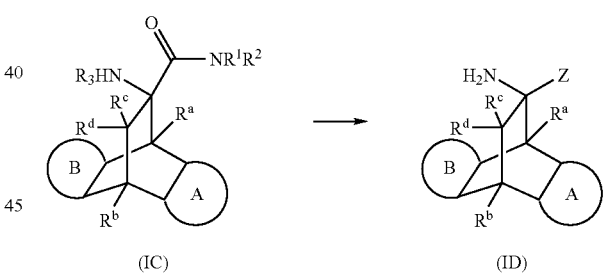

Compound 3 can be converted to the structure of (IA) via hydrolysis using one of the many methods well known to those skilled in the art (such as treatment with concentrated hydrochloride acid in a suitable solvent such as dioxane at reflux).

The starting compound 1 is known in the art and may be commercially available or prepared employing procedures known in the art.

Scheme B

Compounds of formula (IC) of the invention where Z is

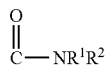

and R$_3$=nitrogen protecting group may be prepared from Compounds of formula (IA) where R$_3$=H, by treatment with an amine-protecting reagent by one of the many methods well known to those skilled in the art (such as treatment of (IA) with di-t-butyl dicarbonate in a solvent of aqueous NaOH and dioxane) to provide compounds of formula (IB). A compound of formula (IB) is then reacted with an amine of formula 4 by one of the many methods of amidation well known to those skilled in the art (such as treatment of compound of formula IB in a suitable solvent such as acetonitrile with diethylaminoethyl chloride hydrochloride (DEC), 1-hydroxy-7-azabenzotriazole, triethylamine and amine 4) to provide compound of formula (IC) of the invention.

Definitions of Terms

Unless otherwise indicated, the term "lower alkyl", "alkyl" or "alk" as employed herein alone or as part of another group includes both straight and branched chain hydrocarbons, containing 1 to 20 carbons, preferably 1 to 10 carbons, more preferably 1 to 8 carbons, in the normal chain, and may optionally include an oxygen or nitrogen in the normal chain. Examples of such chains include methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like, as well as such groups including 1 to 4 substituents such as halo, (including F, Br, Cl or I), CF$_3$, alkoxy, aryl, aryloxy, aryl(aryl) or diaryl, arylalkyl, arylalkyloxy, alkenyl, cycloalkyl, cycloalkylalkyl, cycloalkylalkyloxy, amino, hydroxy, hydroxyalkyl, acyl, heteroaryl, heteroaryloxy, HO—N=, cycloheteroalkyl, alkyloxycarbonyl, alkoxyoximyl, arylheteroaryl, arylalkoxycarbonyl, heteroarylalkyl, heteroarylalkoxy, aryloxyalkyl, aryloxyaryl, alkylamido, alkanoylamino, hydroxyalkyl (alkyl)amino carbonyl, arylcarbonylamino, nitro, cyano, thiol, haloalkyl, trihaloalkyl and/or alkylthio and/or any of the substituents for aryl.

When numbers appear in a subscript after the symbol "C", the subscript defines with more specificity the number of carbon atoms that a particular group may contain. The subscript "0" refers to a bond. When the term "alkyl" is used together with another group, such as in "arylalkyl", this conjunction defines with more specificity at least one of the substituents that the alkyl will contain. For example, "arylalkyl" or "(aryl)alkyl" refers to an alkyl group as defined above where at least one of the substituents is an aryl, such as benzyl. Also, the term aryl($C_{0-4}$)alkyl includes a lower alkyl having at least one aryl substituent and also includes an aryl directly bonded to another group, i.e., aryl($C_0$)alkyl.

Unless otherwise indicated, the term "cycloalkyl" as employed herein alone or as part of another group includes saturated cyclic hydrocarbon groups containing 1 to 3 rings, including monocyclicalkyl, bicyclicalkyl and tricyclicalkyl, containing a total of 3 to 20 carbons forming the rings, preferably 3 to 10 carbons, forming the ring and which may be fused to 1 or 2 aromatic rings (defined below). Accordingly, the term "cycloalkyl" includes groups such as cyclopropyl, cyclobutyl, cyclopentyl, cyclohexyl, cycloheptyl, cyclooctyl, cyclodecyl and cyclododecyl, cyclohexenyl,

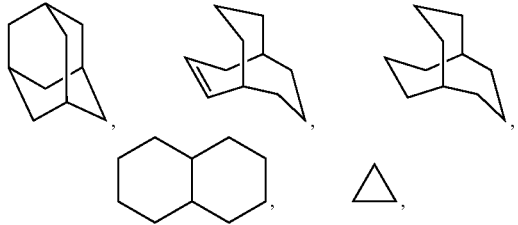

and the like as well as such groups including 1 to 4 substituents such as halogen, alkyl, alkoxy, hydroxy, aryl, aryloxy, arylalkyl, cycloalkyl, alkylamido, alkanoylamino, oxo, acyl, arylcarbonylamino, amino, nitro, cyano, thiol and/or alkylthio and/or any of the substituents for alkyl.

The term "cycloalkenyl" as employed herein alone or as part of another group refers to cyclic hydrocarbons containing 3 to 12 carbons, preferably 5 to 10 carbons and 1 or 2 double bonds. Exemplary cycloalkenyl groups include cyclopentenyl, cyclohexenyl, cycloheptenyl, cyclooctenyl, cyclohexadienyl, and cycloheptadienyl, which may be optionally substituted as defined for cycloalkyl.

The term "cycloalkylene" as employed herein refers to a "cycloalkyl" group which includes free bonds and thus is a linking group such as

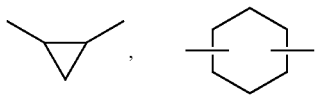

and the like, and may optionally be substituted as defined above for "cycloalkyl".

The term "alkanoyl" as used herein alone or as part of another group refers to alkyl linked to a carbonyl group.

Unless otherwise indicated, the term "lower alkenyl" or "alkenyl" as used herein by itself or as part of another group refers to straight or branched chain radicals of 2 to 20 carbons, preferably 2 to 12 carbons, and more preferably 1 to 8 carbons in the normal chain, which include one to six double bonds in the normal chain, and may optionally include an oxygen or nitrogen in the normal chain. Accordingly, the term "lower alkenyl" or "alkenyl" includes groups such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like as well as such groups including 1 to 4 substituents such as halogen, haloalkyl, alkyl, alkoxy, alkenyl, alkynyl, aryl, arylalkyl, cycloalkyl, amino, hydroxy, heteroaryl, cycloheteroalkyl, alkanoylamino, alkylamido, arylcarbonylamino, nitro, cyano, thiol, alkylthio and/or any of the substituents for alkyl set out herein.

Unless otherwise indicated, the term "lower alkynyl" or "alkynyl" as used herein by itself or as part of another group refers to straight or branched chain radicals of 2 to 20 carbons, preferably 2 to 12 carbons and more preferably 2 to 8 carbons in the normal chain, which include one triple bond in the normal chain, and may optionally include an oxygen or nitrogen in the normal chain. Accordingly, the term "lower alkynyl" or "alkynyl" includes groups such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like as well as such groups including 1 to 4 substituents such as halogen, haloalkyl, alkyl, alkoxy, alkenyl, alkynyl, aryl, arylalkyl, cycloalkyl, amino, heteroaryl, cycloheteroalkyl, hydroxy, alkanoylamino, alkylamido, arylcarbonylamino, nitro, cyano, thiol, and/or alkylthio, and/or any of the substituents for alkyl set out herein.

The terms "arylalkenyl" and "arylalkynyl" as used alone or as part of another group refer to alkenyl and alkynyl groups as described above having an aryl substituent.

The term "alkylene" refers to bivalent straight or branched chain hydrocarbon groups having 1 to 12 carbon atoms, preferably 1 to 8 carbon atoms, e.g., $\{-CH_2-\}_n$, wherein n is 1 to 12, preferably 1-8. Lower alkylene groups, that is, alkylene groups of 1 to 4 carbon atoms, are most preferred, for example "methylene". The terms "alkenylene" and "alkynylene" refer to bivalent radicals of alkenyl and alkynyl groups, respectively, as defined above. When reference is made to a substituted alkenyl, alkynyl, alkylene, alkenylene, or alkynylene group, these groups are substituted with one to three substitutents as defined above for substituted alkyl groups.

Where alkenyl groups as defined above and alkynyl groups as defined above, respectively, have single bonds for attachment at two different carbon atoms, they are termed "alkenylene groups" and "alkynylene groups", respectively, and may optionally be substituted as defined above for "alkenyl" and "alkynyl".

$(CH_2)_p$ and $(CH_2)_q$, includes alkylene, allenyl, alkenylene or alkynylene groups, as defined herein, each of which may optionally include an oxygen or nitrogen in the normal chain, which may optionally include 1, 2, or 3 substituents which include alkyl, alkenyl, halogen, cyano, hydroxy, alkoxy, amino, thioalkyl, keto, $C_3$-$C_6$ cycloalkyl, alkylcarbonylamino or alkylcarbonyloxy; the alkyl substituent may be an alkylene moiety of 1 to 4 carbons which may be attached to one or two carbons in the $(CH_2)_p$ or $(CH_2)_q$ group to form a cycloalkyl group therewith.

Examples of $(CH_2)_p$, $(CH_2)_q$, alkylene, alkenylene and alkynylene include

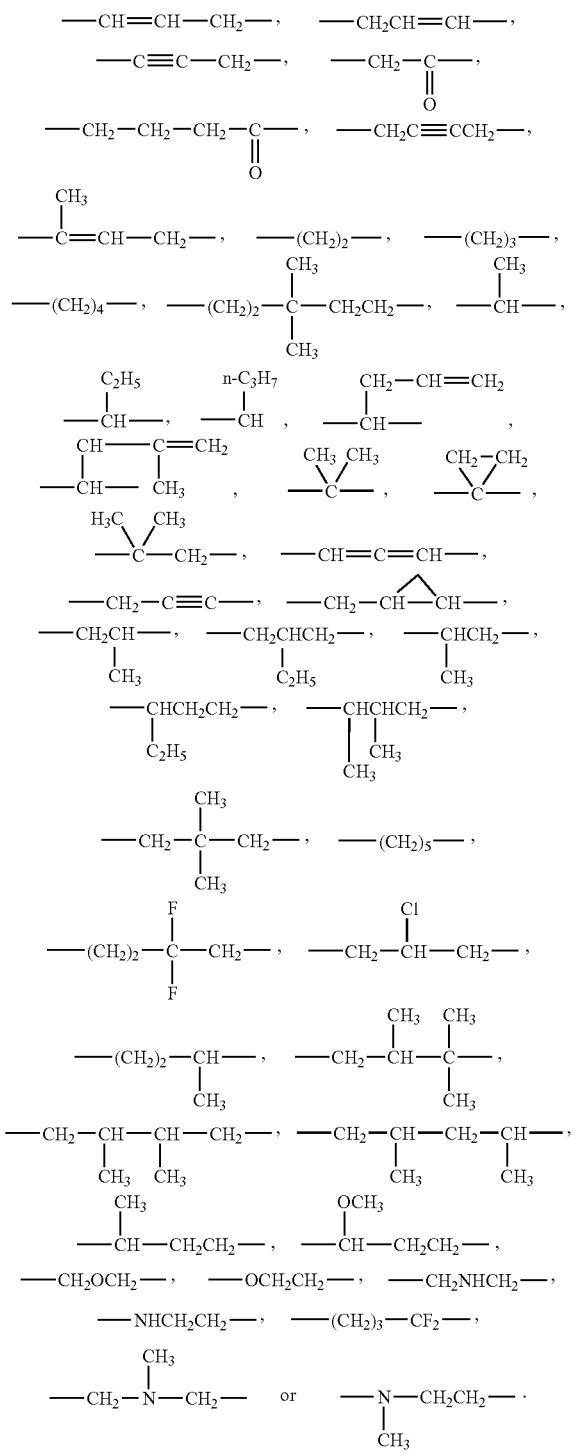

The term "halogen" or "halo" as used herein alone or as part of another group (e.g. $CF_3$ is a haloalkyl group) refers to chlorine, bromine, fluorine, and iodine, with chlorine fluorine or bromine being preferred.

The term "metal ion" refers to alkali metal ions such as sodium, potassium or lithium and alkaline earth metal ions such as magnesium and calcium, as well as zinc and aluminum.

Unless otherwise indicated, the term "aryl", as employed herein alone or as part of another group refers to monocyclic and bicyclic aromatic groups containing 6 to 10 carbons in the ring portion (such as phenyl or naphthyl including 1-naphthyl and 2-naphthyl) and may optionally include one to three additional rings fused to a carbocyclic ring or a heterocyclic ring (such as aryl, cycloalkyl, heteroaryl or cycloheteroalkyl rings. Accordingly, the term "aryl" includes, for example

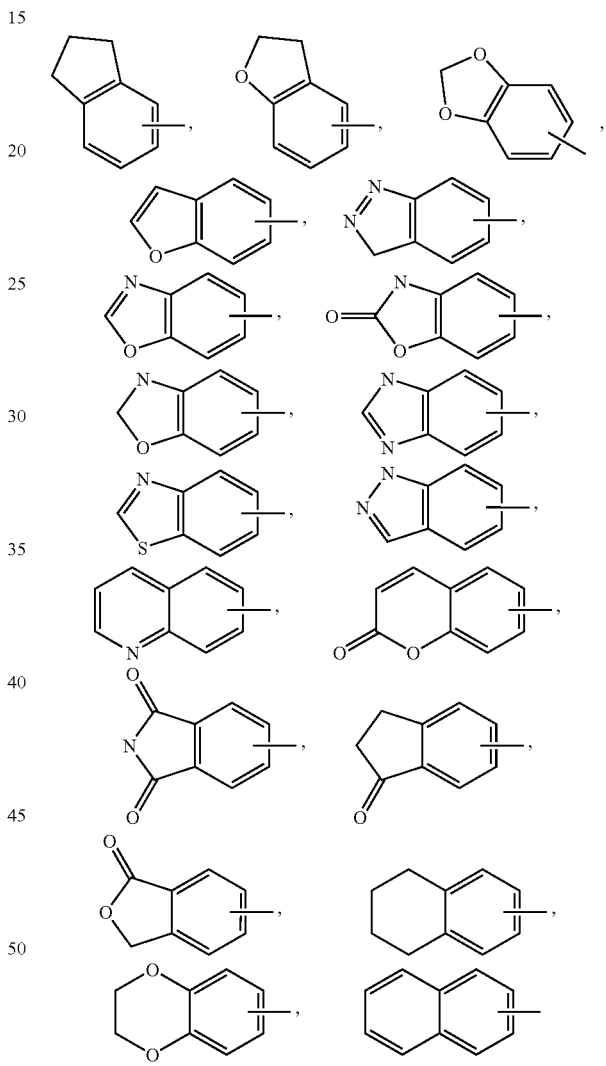

and may be optionally substituted through available carbon atoms with 1, 2, or 3 groups selected from hydrogen, halo, haloalkyl, alkyl, haloalkyl, alkoxy, haloalkoxy, alkenyl, trifluoromethyl, trifluoromethoxy, alkynyl, cycloalkyl-alkyl, cycloheteroalkyl, cycloheteroalkylalkyl, aryl, heteroaryl, arylalkyl, aryloxy, aryloxyalkyl, arylalkoxy, alkoxycarbonyl, arylcarbonyl, arylalkenyl, aminocarbonyl aryl, arylthio, arylsulfinyl, arylazo, heteroarylalkyl, heteroaryl alkenyl, heteroarylheteroaryl, heteroaryloxy, hydroxy, nitro, cyano, amino, substituted amino wherein the amino includes 1 or 2 substituents (which are alkyl, aryl or any of the other aryl compounds mentioned in the definitions), thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino or arylsulfonaminocarbonyl, carboxy, cycloalkyl, arylalkoxy, aryloxycarbonyl, cycloalkylaminocarbonyl, cycloalkylalkylaminocarbonyl, alkoxycarbonylalkyl, alkoxyalkylaminocarbonyl, heteroarylaminocarbonyl, heteroarylalkylaminocarbonyl, arylalkylaminocarbonyl, N-hydroxyalkyl(N-alkyl)aminocarbonyl, cycloheteroalkylaminocarbonyl, cycloheteroalkylalkylaminocarbonyl, N-aryl(N-alkyl)aminocarbonyl, N-arylalkyl(N-cyanoalkyl) aminocarbonyl, dialkylaminoalkylaminocarbonyl, dialkylaminocarbonyl, alkyl-, arylalkyl- or aryl-cycloheteroalkylaminocarbonyl, N-dialkylaminoalkyl(N-alkyl or N-arylalkyl)aminocarbonyl, N-heteroarylalkyl(N-alkyl) aminocarbonyl, N-arylalkyl(N-alkyl)aminocarbonyl, N-dialkylamino(N-arylalkyl)aminocarbonyl, N-hydroxyalkyl(N-arylalkyl)aminocarbonyl, aminoalkyloxycarbonyl, cycloheteroalkylcarbonyl, N=N=N, alkylsulfonyl, aminosulfonyl, heteroarylaminosulfonyl, and/or any of the substituents for alkyl set out herein.

Unless otherwise indicated, the term "lower alkoxy", "alkoxy", "aryloxy" or "aralkoxy" as employed herein alone or as part of another group includes any of the above alkyl, aralkyl or aryl groups linked to an oxygen atom.

Unless otherwise indicated, the term "substituted amino" as employed herein alone or as part of another group refers to amino substituted with one or two substituents, which may be the same or different, such as alkyl, aryl, arylalkyl, heteroaryl, heteroarylalkyl, cycloheteroalkyl, cycloheteroalkylalkyl, cycloalkyl, cycloalkylalkyl, haloalkyl, hydroxyalkyl, alkoxyalkyl or thioalkyl. These substituents may optionally be further substituted with a carboxylic acid and/or any of the substituents for alkyl as set out above. In addition, the amino substituents may be taken together with the nitrogen atom to which they are attached to form 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl, 1-pyrrolidinyl, 1-piperidinyl, or 1-azepinyl, optionally substituted with alkyl, alkoxy, alkylthio, halo, trifluoromethyl or hydroxy.

Unless otherwise indicated, the term "lower alkylthio", "alkylthio", "arylthio" or "aralkylthio" as employed herein alone or as part of another group includes any of the above alkyl, aralkyl or aryl groups linked to a sulfur atom.

Unless otherwise indicated, the term "acyl" as employed herein by itself or part of another group, as defined herein, refers to an organic radical linked to a carbonyl

group; examples of acyl groups include any of the R groups attached to a carbonyl, such as alkanoyl, alkenoyl, aroyl, aralkanoyl, heteroaroyl, cycloalkanoyl, cycloheteroalkanoyl and the like.

Unless otherwise indicated, the term "lower alkylamino", "alkylamino", "acylamino", "arylamino", or "arylalkylamino" as employed herein alone or as part of another group includes any of the above alkyl, aryl or arylalkyl acyl groups linked to a nitrogen atom. The term "acylamino", for example, includes the group —NHC(O)alkyl.

Unless otherwise indicated, the term "cycloheteroalkyl" as used herein alone or as part of another group refers to a 5-, 6- or 7-membered saturated or partially unsaturated ring which includes 1 to 2 hetero atoms such as nitrogen, oxygen and/or sulfur, linked through a carbon atom or a heteroatom, where possible, optionally via the linker $(CH_2)_p$ (where p is 0, 1, 2 or 3), such as

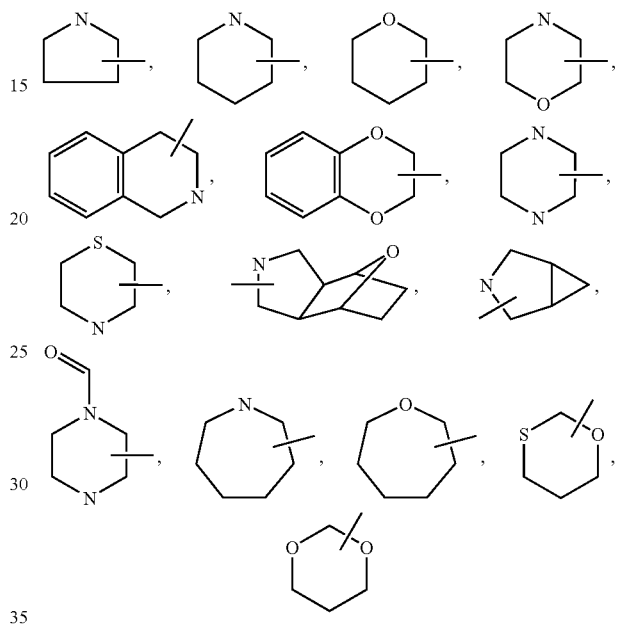

and the like. The above groups may include 1 to 4 substituents such as alkyl, halo, oxo and/or any of the substituents for alkyl or aryl set out herein. In addition, any of the cycloheteroalkyl rings can be fused to a cycloalkyl, aryl, heteroaryl or cycloheteroalkyl ring.

Unless otherwise indicated, the term "heteroaryl" as used herein alone or as part of another group refers to a 5-, 6- or 7-membered aromatic ring which includes 1, 2, 3 or 4 hetero atoms such as nitrogen, oxygen or sulfur, and such rings fused to an aryl, cycloalkyl, heteroaryl or cycloheteroalkyl ring (e.g. benzothiophenyl, indolyl), and includes possible N-oxides, linked through a carbon atom or a heteroatom, where possible, optionally via the linker $(CH_2)_q$ (where q is 0, 1, 2 or 3). The heteroaryl group may optionally include 1 to 4 substituents such as any of the substituents for alkyl or aryl set out above. Examples of heteroaryl groups include the following:

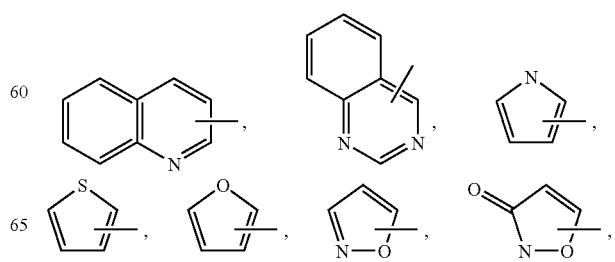

-continued

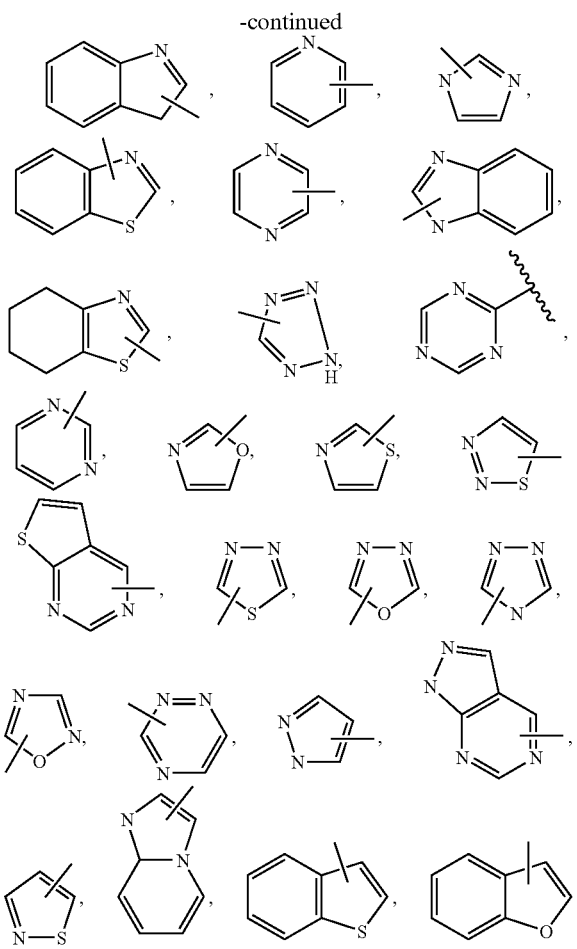

and the like.

The term "cycloheteroalkylalkyl" as used herein alone or as part of another group refers to cycloheteroalkyl groups as defined above linked through a C atom or heteroatom to a $(CH_2)_p$ chain.

The term "heteroarylalkyl" or "heteroaryl alkenyl" as used herein alone or as part of another group refers to a heteroaryl group as defined above linked through a C atom or heteroatom to a —$(CH_2)_q$— chain, alkylene or alkenylene as defined above.

The term "polyhaloalkyl" as used herein refers to an "alkyl" group as defined above which includes from 2 to 9, preferably from 2 to 5, halo substituents, such as F or Cl, preferably F, such as $CF_3CH_2$, $CF_3$ or $CF_3CF_2CH_2$.

The term "polyhaloalkyloxy" as used herein refers to an "alkoxy" or "alkyloxy" group as defined above which includes from 2 to 9, preferably from 2 to 5, halo substituents, such as F or Cl, preferably F, such as $CF_3H_2O$, $CF_3O$ or $CF_3F_2CH_2O$.

The term "prodrug" denotes a compound which, upon administration to a subject, undergoes chemical conversion by metabolic or chemical processes to yield a compound of the formula (I), and/or a salt and/or solvate thereof. For example, compounds containing a carboxy group can form physiologically hydrolyzable esters which serve as prodrugs by being hydrolyzed in the body to yield formula (I) compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula (I) include $C_{1-6}$alkylbenzyl, 4-methoxybenzyl, indanyl, phthalyl, methoxymethyl, $C_{1-6}$alkanoyloxy-$C_{1-6}$alkyl, e.g. acetoxymethyl, pivaloyloxymethyl or propionyloxymethyl, $C_{1-6}$alkoxycarbonyloxy-$C_{1-6}$alkyl, e.g. methoxycarbonyl-oxymethyl or ethoxycarbonyloxymethyl, glycyloxymethyl, phenylglycyloxymethyl, (5-methyl-2-oxo-1,3-dioxolen-4-yl)-methyl and other well known physiologically hydrolyzable esters used, for example, in the penicillin and cephalosporin arts. Such esters may be prepared by conventional techniques known in the art.

Prodrug ester examples include the following groups: (1-alkanoyloxy)alkyl such as,

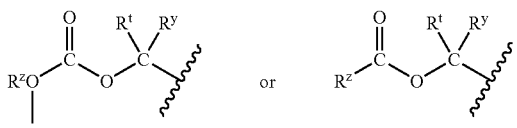

wherein $R^z$, $R^t$ and $R^y$ are H, alkyl, aryl or arylalkyl; however, $R^zO$ cannot be HO.

Examples of such prodrug esters include

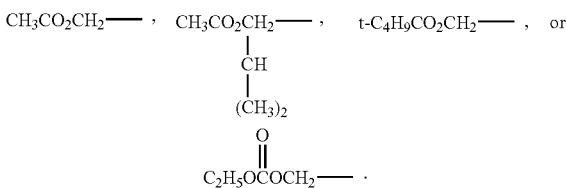

Other examples of suitable prodrug esters include

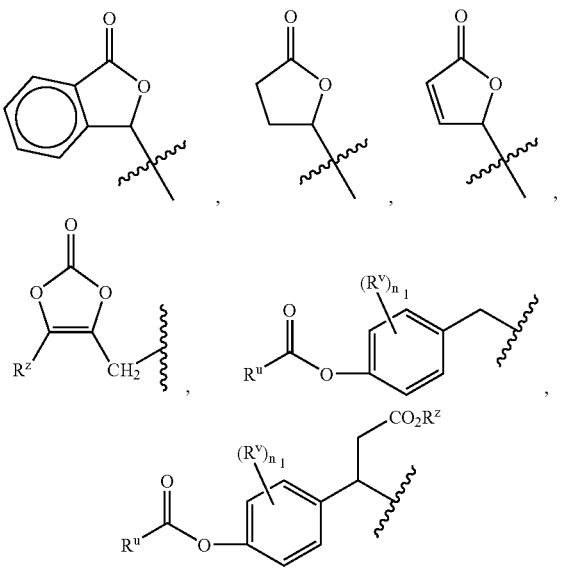

wherein $R^z$ can be H, alkyl (such as methyl or t-butyl), arylalkyl (such as benzyl) or aryl (such as phenyl); $R^v$ is H, alkyl, halogen or alkoxy, $R^u$ is alkyl, aryl, arylalkyl or alkoxyl, and $n_1$ is 0, 1 or 2.

For further examples of prodrug derivatives, see:

a) *Design of Prodrugs*, edited by H. Bundgaard, (Elsevier, 1985) and *Methods in Enzymology*, Vol. 42, p. 309-396, edited by K. Widder, et al. (Acamedic Press, 1985);

b) *A Textbook of Drug Design and Development*, edited by Krosgaard-Larsen and H. Bundgaard, Chapter 5, "Design and Application of Prodrugs," by H. Bundgaard, pp. 113-191 (1991); and c) H. Bundgaard, *Advanced Drug Delivery Reviews*, 8, 1-38 (1992).

The term "tautomer" refers to compounds of the formula (I) and salts thereof that may exist in their tautomeric form, in which hydrogen atoms are transposed to other parts of the molecules and the chemical bonds between the atoms of the molecules are consequently rearranged. It should be understood that the all tautomeric forms, insofar as they may exist, are included within the invention.

The terms pharmaceutically acceptable "salt" and "salts" refer to basic salts formed with inorganic and organic bases. Such salts include ammonium salts; alkali metal salts, such as lithium, sodium and potassium salts (which are preferred); alkaline earth metal salts, such as calcium and magnesium salts; salts with organic bases, such as amine like salts (e.g., dicyclohexylamine salt, benzathine, N-methyl-D-glucamine, and hydrabamine salts); and salts with amino acids like arginine, lysine and the like; and zwitterions, the so-called "inner salts". Nontoxic, pharmaceutically acceptable salts are preferred, although other salts are also useful, e.g., in isolating or purifying the product.

The term pharmaceutically acceptable "salt" and "salts" also includes acid addition salts. These are formed, for example, with strong inorganic acids, such as mineral acids, for example sulfuric acid, phosphoric acid or a hydrohalic acid such as HCl or HBr, with strong organic carboxylic acids, such as alkanecarboxylic acids of 1 to 4 carbon atoms which are unsubstituted or substituted, for example, by halogen, for example acetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic or glutamic acid or lysine or arginine), or benzoic acid, or with organic sulfonic acids, such as (C1-C4) alkyl or arylsulfonic acids which are unsubstituted or substituted, for example by halogen, for example methanesulfonic acid or p-toluenesulfonic acid.

All stereoisomers of the compounds of the instant invention are contemplated, either in admixture or in pure or substantially pure form. The compounds of the present invention can have asymmetric centers at any of the carbon atoms including any one or the R substituents. Consequently, compounds of formula I can exist in enantiomeric or diastereomeric forms or in mixtures thereof. The processes for preparation can utilize racemates, enantiomers or diastereomers as starting materials. When diastereomeric or enantiomeric products are prepared, they can be separated by conventional methods for example, chromatographic or fractional crystallization.

The inventive compounds may be in the free or solvate (e.g. hydrate) form.

Combinations

Where desired, the compounds of structure I may be used in combination with one or more other types of therapeutic agents such as immunosuppressants, anticancer agents, antiviral agents, anti-inflammatory agents, anti-fungal agents, antibiotics, anti-vascular hyperproliferation agents, anti-depressive agents, hypolipidemic agents or lipid-lowering agents or lipid modulating agents, antidiabetic agents, anti-obesity agents, antihypertensive agents, platelet aggregation inhibitors, and/or anti-osteoporosis agents, which may be administered orally in the same dosage form, in a separate oral dosage form or by injection.

The immunosuppressants which may be optionally employed in combination with compounds of formula I of the invention include cyclosporins, for example cyclosporin A, mycophenolate, interferon-beta, deoxyspergolin, FK-506 or Ant.-IL-2.

The anti-cancer agents which may be optionally employed in combination with compounds of formula I of the invention include azathiprine, 5-fluorouracil, cyclophosphamide, cisplatin, methotrexate, thiotepa, carboplatin, and the like.

The anti-viral agents which may be optionally employed in combination with compounds of formula I of the invention include abacavir, aciclovir, ganciclovir, zidanocin, vidarabine, and the like.

The anti-inflammatory agents which may be optionally employed in combination with compounds of formula I of the invention include non-steroidal anti-inflammatory drugs (NSAIDs) such as ibuprofen, cox-2 inhibitors such as celecoxib, rofecoxib, aspirin, naproxen, ketoprofen, diclofenac sodium, indomethacin, piroxicam, steroids such as prednisone, dexamethasone, hydrocortisone, triamcinolone diacetate, gold compounds, such as gold sodium thiomalate, TNF-α inhibitors such as tenidap, anti-TNF antibodies or soluble TNF receptor, and rapamycin (sirolimus or Rapamune) or derivatives thereof, infliximab (Remicade® Centocor, Inc.). CTLA-4Ig, LEA29Y, antibodies such as anti-ICAM-3, anti-IL-2 receptor (Anti-Tac), anti-CD45RB, anti-CD2, anti-CD3 (OKT-3), anti-CD4, anti-CD80, anti-CD86, monoclonal antibody OKT3, agents blocking the interaction between CD40 and CD154 (a.k.a. "gp39"), such as antibodies specific for CD40 and/or CD154, fusion proteins such as etanercept, fusion proteins constructed from CD40 and/or CD154gp39 (e.g. CD40Ig and CD8gp39), inhibitors, such as nuclear translocation inhibitors, of NF-kappa B function, such as deoxyspergualin (DSG).

The anti-fungal agents which may be optionally employed in combination with compounds of formula I of the invention include fluconazole, miconazole, amphotericin B, and the like.

The antibiotics which may be optionally employed in combination with compounds of formula I of the invention include penicillin, tetracycline, amoxicillin, ampicillin, erythromycin, doxycycline, vancomycin, minocycline, clindamycin or cefalexin.

The anti-vascular hyperproliferation agents which may be optionally employed with compounds of formula I of the invention include methotrexate, leflunomide, FK506 (tacrolimus, Prograf), The hypolipidemic agent or lipid-lowering agent or lipid modulating agents which may be optionally employed in combination with the compounds of formula I of the invention may include 1, 2, 3 or more MTP inhibitors, HMG CoA reductase inhibitors, squalene synthetase inhibitors, fibric acid derivatives, ACAT inhibitors, lipoxygenase inhibitors, cholesterol absorption inhibitors, ileal Na+/bile acid cotransporter inhibitors, upregulators of LDL receptor activity, bile acid sequestrants, and/or nicotinic acid and derivatives thereof.

MTP inhibitors employed herein include MTP inhibitors disclosed in U.S. Pat. No. 5,595,872, U.S. Pat. No. 5,739,135, U.S. Pat. No. 5,712,279, U.S. Pat. No. 5,760,246, U.S. Pat. No. 5,827,875, U.S. Pat. No. 5,885,983 and U.S. application Ser. No. 09/175,180 filed Oct. 20, 1998, now U.S. Pat. No. 5,962,440. Preferred are each of the preferred MTP inhibitors disclosed in each of the above patents and applications.

All of the above U.S. patents and applications are incorporated herein by reference.

Most preferred MTP inhibitors to be employed in accordance with the present invention include preferred MTP inhibitors as set out in U.S. Pat. Nos. 5,739,135 and 5,712,279, and U.S. Pat. No. 5,760,246.

The most preferred MTP inhibitor is 9-[4-[4-[[2-(2,2,2-trifluoroethoxy)benzoyl]amino]-1-piperidinyl]butyl]-N-(2,2,2-trifluoroethyl)-9H-fluorene-9-carboxamide

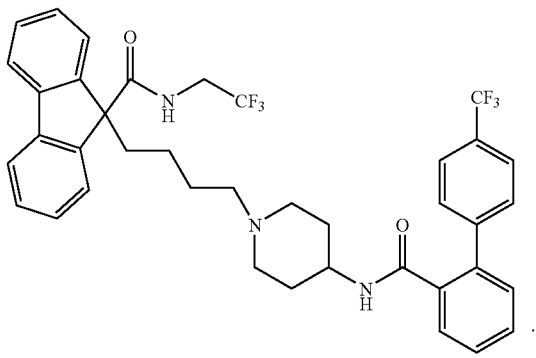

The hypolipidemic agent may be an HMG CoA reductase inhibitor which includes, but is not limited to, mevastatin and related compounds as disclosed in U.S. Pat. No. 3,983,140, lovastatin (mevinolin) and related compounds as disclosed in U.S. Pat. No. 4,231,938, pravastatin and related compounds such as disclosed in U.S. Pat. No. 4,346,227, simvastatin and related compounds as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354,772, cerivastatin disclosed in U.S. Pat. Nos. 5,006,530 and 5,177,080, atorvastatin disclosed in U.S. Pat. Nos. 4,681,893, 5,273,995, 5,385,929 and 5,686,104, itavastatin (Nissan/Sankyo's nisvastatin (NK-104)) disclosed in U.S. Pat. No. 5,011,930, Shionogi-Astra/Zeneca visastatin (ZD-4522) disclosed in U.S. Pat. No. 5,260,440, and related statin compounds disclosed in U.S. Pat. No. 5,753,675, pyrazole analogs of mevalonolactone derivatives as disclosed in U.S. Pat. No. 4,613,610, indene analogs of mevalonolactone derivatives as disclosed in PCT application WO 86/03488, 6-[2-(substituted-pyrrol-1-yl)-alkyl)pyran-2-ones and derivatives thereof as disclosed in U.S. Pat. No. 4,647,576, Searle's SC-45355 (a 3-substituted pentanedioic acid derivative) dichloroacetate, imidazole analogs of mevalonolactone as disclosed in PCT application WO 86/07054, 3-carboxy-2-hydroxy-propane-phosphonic acid derivatives as disclosed in French Patent No. 2,596,393, 2,3-disubstituted pyrrole, furan and thiophene derivatives as disclosed in European Patent Application No. 0221025, naphthyl analogs of mevalonolactone as disclosed in U.S. Pat. No. 4,686,237, octahydronaphthalenes such as disclosed in U.S. Pat. No. 4,499,289, keto analogs of mevinolin (lovastatin) as disclosed in European Patent Application No. 0,142,146 A2, and quinoline and pyridine derivatives disclosed in U.S. Pat. Nos. 5,506,219 and 5,691,322.

In addition, phosphinic acid compounds useful in inhibiting HMG CoA reductase suitable for use herein are disclosed in GB 2205837.

The squalene synthetase inhibitors suitable for use herein include, but are not limited to, α-phosphono-sulfonates disclosed in U.S. Pat. No. 5,712,396, those disclosed by Biller et al, J. Med. Chem., Vol. 31, No. 10, pp 1869-1871 (1988), including isoprenoid (phosphinyl-methyl)phosphonates as well as other known squalene synthetase inhibitors, for example, as disclosed in U.S. Pat. Nos. 4,871,721 and 4,924,024 and in Biller, S. A., Neuenschwander, K., Ponpipom, M. M., and Poulter, C. D., Current Pharmaceutical Design, 2, 1-40 (1996).

In addition, other squalene synthetase inhibitors suitable for use herein include the terpenoid pyrophosphates disclosed by P. Ortiz de Montellano et al, J. Med. Chem., 1977, 20, 243-249, the farnesyl diphosphate analog A and presqualene pyrophosphate (PSQ-PP) analogs as disclosed by Corey and Volante, J. Am. Chem. Soc., 98, 1291-1293 (1976), phosphinylphosphonates reported by McClard, R. W. et al, J. Am. Chem. Soc., 1987, 109, 5544 (1987), and cyclopropanes reported by Capson, T. L., PhD dissertation, Dept. Med. Chem. U of Utah, Abstract, Table of Contents, pp 16, 17, 40-43, 48-51, Summary (June, 1987).

Other hypolipidemic agents suitable for use herein include, but are not limited to, fibric acid derivatives, such as fenofibrate, gemfibrozil, clofibrate, bezafibrate, ciprofibrate, clinofibrate and the like, probucol, and related compounds as disclosed in U.S. Pat. No. 3,674,836, probucol and gemfibrozil being preferred, bile acid sequestrants such as cholestyramine, colestipol and DEAE-Sephadex (Secholex®, Policexide®) and cholestagel (Sankyo/Geltex), as well as lipostabil (Rhone-Poulenc), Eisai E-5050 (an N-substituted ethanolamine derivative), imanixil (HOE-402), tetrahydrolipstatin (THL), istigmastanylphos-phorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid (niacin), acipimox, acifran, neomycin, p-aminosalicylic acid, aspirin, poly(diallylmethylamine) derivatives such as disclosed in U.S. Pat. No. 4,759,923, quaternary amine poly(diallyldimethylammonium chloride) and ionenes such as disclosed in U.S. Pat. No. 4,027,009, and other known serum cholesterol lowering agents.

The hypolipidemic agent may be an ACAT inhibitor such as disclosed in, Drugs of the Future 24, 9-15 (1999), (Avasimibe); "The ACAT inhibitor, C1-1011 is effective in the prevention and regression of aortic fatty streak area in hamsters", Nicolosi et al, Atherosclerosis (Shannon, Irel). 137(1), 77-85 (1998) "The pharmacological profile of FCE 27677: a novel ACAT inhibitor with potent hypolipidemic activity mediated by selective suppression of the hepatic secretion of ApoB100-containing lipoprotein", Ghiselli, Giancarlo, Cardiovasc. Drug Rev. (1998), 16(1), 16-30; "RP 73163: a bioavailable alkylsulfinyl-diphenylimidazole ACAT inhibitor", Smith, C., et al, Bioorg. Med. Chem. Lett. 6(1), 47-50 (1996); "ACAT inhibitors: physiologic mechanisms for hypolipidemic and anti-atherosclerotic activities in experimental animals", Krause et al, Editor(s): Ruffolo, Robert R., Jr.; Hollinger, Mannfred A., Inflammation:

*Mediators Pathways* 173-98 (1995), Publisher: CRC, Boca Raton, Fla.; "ACAT inhibitors: potential anti-atherosclerotic agents", Sliskovic et al, *Curr. Med. Chem.* 1(3), 204-25 (1994); "Inhibitors of acyl-CoA:cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl)methyl]ureas with enhanced hypocholesterolemic activity", Stout et al, *Chemtracts: Org. Chem.* 8(6), 359-62 (1995), or TS-962 (Taisho Pharmaceutical Co. Ltd).

The hypolipidemic agent may be an upregulator of LD2 receptor activity such as MD-700 (Taisho Pharmaceutical Co. Ltd) and LY295427 (Eli Lilly).

The hypolipidemic agent may be a cholesterol absorption inhibitor preferably Schering-Plough's ezetimibe (SCH58235) and SCH48461 as well as those disclosed in *Atherosclerosis* 115, 45-63 (1995) and *J. Med. Chem.* 41, 973 (1998).

The hypolipidemic agent may be an ileal $Na^+$/bile acid cotransporter inhibitor such as disclosed in *Drugs of the Future,* 24, 425-430 (1999).

The lipid-modulating agent may be a cholesteryl ester transfer protein (CETP) inhibitor such as Pfizer's CP 529, 414 (WO/0038722 and EP 818448) and Pharmacia's SC-744 and SC-795.

The ATP citrate lyase inhibitor which may be employed in the combination of the invention may include, for example, those disclosed in U.S. Pat. No. 5,447,954.

Preferred hypolipidemic agents are pravastatin, lovastatin, simvastatin, atorvastatin, fluvastatin, cerivastatin, itavastatin and visastatin and ZD-4522.

The above-mentioned U.S. patents are incorporated herein by reference. The amounts and dosages employed will be as indicated in the Physician's Desk Reference and/or in the patents set out above.

The compounds of formula I of the invention will be employed in a weight ratio to the hypolipidemic agent (were present), within the range from about 500:1 to about 1:500, preferably from about 100:1 to about 1:100.

The dose administered must be carefully adjusted according to age, weight and condition of the patient, as well as the route of administration, dosage form and regimen and the desired result.

The dosages and formulations for the hypolipidemic agent will be as disclosed in the various patents and applications discussed above.

The dosages and formulations for the other hypolipidemic agent to be employed, where applicable, will be as set out in the latest edition of the Physicians' Desk Reference.

For oral administration, a satisfactory result may be obtained employing the MTP inhibitor in an amount within the range of from about 0.01 mg to about 500 mg and preferably from about 0.1 mg to about 100 mg, one to four times daily.

A preferred oral dosage form, such as tablets or capsules, will contain the MTP inhibitor in an amount of from about 1 to about 500 mg, preferably from about 2 to about 400 mg, and more preferably from about 5 to about 250 mg, one to four times daily.

For oral administration, a satisfactory result may be obtained employing an HMG CoA reductase inhibitor, for example, pravastatin, lovastatin, simvastatin, atorvastatin, fluvastatin or cerivastatin in dosages employed as indicated in the Physician's Desk Reference, such as in an amount within the range of from about 1 to 2000 mg, and preferably from about 4 to about 200 mg.

The squalene synthetase inhibitor may be employed in dosages in an amount within the range of from about 10 mg to about 2000 mg and preferably from about 25 mg to about 200 mg.

A preferred oral dosage form, such as tablets or capsules, will contain the HMG CoA reductase inhibitor in an amount from about 0.1 to about 100 mg, preferably from about 0.5 to about 80 mg, and more preferably from about 1 to about 40 mg.

A preferred oral dosage form, such as tablets or capsules will contain the squalene synthetase inhibitor in an amount of from about 10 to about 500 mg, preferably from about 25 to about 200 mg.

The hypolipidemic agent may also be a lipoxygenase inhibitor including a 15-lipoxygenase (15-LO) inhibitor such as benzimidazole derivatives as disclosed in WO 97/12615, 15-LO inhibitors as disclosed in WO 97/12613, isothiazolones as disclosed in WO 96/38144, and 15-LO inhibitors as disclosed by Sendobry et al "Attenuation of diet-induced atherosclerosis in rabbits with a highly selective 15-lipoxygenase inhibitor lacking significant antioxidant properties", *Brit. J. Phannacology* 120, 1199-1206 (1997), and Comicelli et al, "15-Lipoxygenase and its Inhibition: A Novel Therapeutic Target for Vascular Disease", *Current Pharmaceutical Design,* 5, 11-20 (1999).

The compounds of formula I and the hypolipidemic agent may be employed together in the same oral dosage form or in separate oral dosage forms taken at the same time.

The compositions described above may be administered in the dosage forms as described above in single or divided doses of one to four times daily. It may be advisable to start a patient on a low dose combination and work up gradually to a high dose combination.

The preferred hypolipidemic agent is pravastatin, simvastatin, lovastatin, atorvastatin, fluvastatin or cerivastatin as well as niacin and/or cholestagel.

The other antidiabetic agent which may be optionally employed in combination with the compound of formula I may be 1, 2, 3 or more antidiabetic agents or antihyperglycemic agents including insulin secretagogues or insulin sensitizers, or other antidiabetic agents preferably having a mechanism of action different from the compounds of formula I of the invention, which may include biguanides, sulfonyl ureas, glucosidase inhibitors, PPAR γ agonists, such as thiazolidinediones, aP2 inhibitors, dipeptidyl peptidase IV (DP4) inhibitors, SGLT2 inhibitors, and/or meglitinides, as well as insulin, and/or glucagon-like peptide-1 (GLP-1).

The other antidiabetic agent may be an oral antihyperglycemic agent preferably a biguanide such as metformin or phenformin or salts thereof, preferably metformin HCl.

Where the antidiabetic agent is a biguanide, the compounds of structure I will be employed in a weight ratio to biguanide within the range from about 0.001:1 to about 10:1, preferably from about 0.01:1 to about 5:1.

The other antidiabetic agent may also preferably be a sulfonyl urea such as glyburide (also known as glibenclamide), glimepiride (disclosed in U.S. Pat. No. 4,379,785), glipizide, gliclazide or chlorpropamide, other known sulfonylureas or other antihyperglycemic agents which act on the ATP-dependent channel of the □-cells, with glyburide and glipizide being preferred, which may be administered in the same or in separate oral dosage forms.

The compounds of structure I will be employed in a weight ratio to the sulfonyl urea in the range from about 0.01:1 to about 100:1, preferably from about 0.02:1 to about 5:1.

The oral antidiabetic agent may also be a glucosidase inhibitor such as acarbose (disclosed in U.S. Pat. No. 4,904,769) or miglitol (disclosed in U.S. Pat. No. 4,639,436), which may be administered in the same or in a separate oral dosage forms.

The compounds of structure I will be employed in a weight ratio to the glucosidase inhibitor within the range from about 0.01:1 to about 100:1, preferably from about 0.05:1 to about 10:1.

The compounds of structure I may be employed in combination with a PPAR γ agonist such as a thiazolidinedione oral anti-diabetic agent or other insulin sensitizers (which has an insulin sensitivity effect in NIDDM patients) such as troglitazone (Warner-Lambert's Rezulin®, disclosed in U.S. Pat. No. 4,572,912), rosiglitazone (SKB), pioglitazone (Takeda), Mitsubishi's MCC-555 (disclosed in U.S. Pat. No. 5,594,016), Glaxo-Welcome's GL-262570, englitazone (CP-68722, Pfizer) or darglitazone (CP-86325, Pfizer, isaglitazone (MIT/J&J), JTT-501 (JPNT/P&U), L-895645 (Merck), R-119702 (Sankyo/WL), NN-2344 (Dr. Reddy/NN), or YM-440 (Yamanouchi), preferably rosiglitazone and pioglitazone.

The compounds of structure I will be employed in a weight ratio to the thiazolidinedione in an amount within the range from about 0.01:1 to about 100:1, preferably from about 0.05 to about 10:1.

The sulfonyl urea and thiazolidinedione in amounts of less than about 150 mg oral antidiabetic agent may be incorporated in a single tablet with the compounds of structure I.

The compounds of structure I may also be employed in combination with a antihyperglycemic agent such as insulin or with glucagon-like peptide-1 (GLP-1) such as GLP-1(1-36) amide, GLP-1(7-36) amide, GLP-1(7-37) (as disclosed in U.S. Pat. No. 5,614,492 to Habener, the disclosure of which is incorporated herein by reference), as well as AC2993 (Amylin) and LY-315902 (Lilly), which may be administered via injection, intranasal, inhalation or by transdermal or buccal devices.

Where present, metformin, the sulfonyl ureas, such as glyburide, glimepiride, glipyride, glipizide, chlorpropamide and gliclazide and the glucosidase inhibitors acarbose or miglitol or insulin (injectable, pulmonary, buccal, or oral) may be employed in formulations as described above and in amounts and dosing as indicated in the Physician's Desk Reference (PDR).

Where present, metformin or salt thereof may be employed in amounts within the range from about 500 to about 2000 mg per day which may be administered in single or divided doses one to four times daily.

Where present, the thiazolidinedione anti-diabetic agent may be employed in amounts within the range from about 0.01 to about 2000 mg/day which may be administered in single or divided doses one to four times per day.

Where present insulin may be employed in formulations, amounts and dosing as indicated by the Physician's Desk Reference.

Where present GLP-1 peptides may be administered in oral buccal formulations, by nasal administration or parenterally as described in U.S. Pat. No. 5,346,701 (TheraTech), U.S. Pat. Nos. 5,614,492 and 5,631,224 which are incorporated herein by reference.

The other antidiabetic agent may also be a PPAR α/γ dual agonist such as AR-HO39242 (Astra/Zeneca), GW-409544 (Glaxo-Wellcome), KRP297 (Kyorin Merck) as well as those disclosed by Murakarni et al, "A Novel Insulin Sensitizer Acts As a Coligand for Peroxisome Proliferation-Activated Receptor Alpha (PPAR alpha) and PPAR gamma. Effect on PPAR alpha Activation on Abnormal Lipid Metabolism in Liver of Zucker Fatty Rats", *Diabetes* 47, 1841-1847 (1998).

The antidiabetic agent may be an SGLT2 inhibitor such as disclosed in U.S. application Ser. No. 09/679,027, filed Oct. 4, 2000 employing dosages as set out therein. Preferred are the compounds designated as preferred in the above application.

The antidiabetic agent may be an aP2 inhibitor such as disclosed in U.S. application Ser. No. 09/391,053, filed Sep. 7, 1999, and in U.S. application Ser. No. 09/519,079, filed Mar. 6, 2000 employing dosages as set out herein. Preferred are the compounds designated as preferred in the above application.

The antidiabetic agent may be a DP4 inhibitor such as disclosed in U.S. application Ser. No. 09/788,173 filed Feb. 16, 2001, WO99/38501, WO99/46272, WO99/67279 (PROBIODRUG), WO99/67278 (PROBIODRUG), WO99/61431 (PROBIODRUG), NVP-DPP728A (1-[[[2-[(5-cyanopyridin-2-yl)amino]ethyl]amino]acetyl]-2-cyano-(S)-pyrrolidine) (Novartis) (preferred) as disclosed by Hughes et al, *Biochemistry*, 38(36), 11597-11603, (1999), TSL-225 (tryptophyl-1,2,3,4-tetrahydro-isoquinoline-3-carboxylic acid (disclosed by Yamada et al, *Bioorg. & Med. Chem. Lett.* 8 1537-1540 (1998), 2-cyanopyrrolidides and 4-cyanopyrrolidides as disclosed by Ashworth et al, *Bioorg. & Med. Chem. Lett.*, Vol. 6, No. 22, pp 1163-1166 and 2745-2748 (1996) employing dosages as set out in the above references.

The meglitinide which may optionally be employed in combination with the compound of formula I of the invention may be repaglinide, nateglinide (Novartis) or KAD1229 (PF/Kissei), with repaglinide being preferred.

The compound of formula I will be employed in a weight ratio to the meglitinide, PPAR γ agonist, PPAR α/γ dual agonist, aP2 inhibitor, DP4 inhibitor or SGLT2 inhibitor within the range from about 0.01:1 to about 100:1, preferably from about 0.05 to about 10:1.

The other type of therapeutic agent which may be optionally employed with a compound of formula I may be 1, 2, 3 or more of an anti-obesity agent including a beta 3 adrenergic agonist, a lipase inhibitor, a serotonin (and dopamine) reuptake inhibitor, an aP2 inhibitor, a thyroid receptor agonist and/or an anorectic agent.

The beta 3 adrenergic agonist which may be optionally employed in combination with a compound of formula I may be AJ9677 (Takeda/Dainippon), L750355 (Merck), or CP331648 (Pfizer) or other known beta 3 agonists as disclosed in U.S. Pat. Nos. 5,541,204, 5,770,615, 5,491,134, 5,776,983 and 5,488,064, with AJ9677, L750,355 and CP331648 being preferred.

The lipase inhibitor which may be optionally employed in combination with a compound of formula I may be orlistat or ATL-962 (Alizyme), with orlistat being preferred.

The serotonin (and dopoamine) reuptake inhibitor which may be optionally employed in combination with a compound of formula I may be sibutramine, topiramate (Johnson & Johnson) or axokine (Regeneron), with sibutramine and topiramate being preferred.

The thyroid receptor agonist which may be optionally employed in combination with a compound of formula I may be a thyroid receptor ligand as disclosed in WO97/

21993 (U. Cal SF), WO99/00353 (KaroBio), GB98/284425 (KaroBio), and U.S. Provisional Application 60/183,223 filed Feb. 17, 2000, with compounds of the KaroBio applications and the above U.S. provisional application being preferred.

The anorectic agent which may be optionally employed in combination with a compound of formula I may be dexamphetamine, phentermine, phenylpropanolamine or mazindol, with dexamphetamine being preferred.

The various anti-obesity agents described above may be employed in the same dosage form with the compound of formula I or in different dosage forms, in dosages and regimens as generally known in the art or in the PDR.

The antihypertensive agents which may be employed in combination with the compound of formula I of the invention include ACE inhibitors, angiotensin II receptor antagonists, NEP/ACE inhibitors, as well as calcium channel blockers, β-adrenergic blockers and other types of antihypertensive agents including diuretics.

The angiotensin converting enzyme inhibitor which may be employed herein includes those containing a mercapto (—S—) moiety such as substituted proline derivatives, such as any of those disclosed in U.S. Pat. No. 4,046,889 to Ondetti et al mentioned above, with captopril, that is, 1-[(2S)-3-mercapto-2-methylpropionyl]-L-proline, being preferred, and mercaptoacyl derivatives of substituted prolines such as any of those disclosed in U.S. Pat. No. 4,316,906 with zofenopril being preferred.

Other examples of mercapto containing ACE inhibitors that may be employed herein include rentiapril (fentiapril, Santen) disclosed in Clin. Exp. Pharmacol. Physiol. 10:131 (1983); as well as pivopril and YS980.

Other examples of angiotensin converting enzyme inhibitors which may be employed herein include any of those disclosed in U.S. Pat. No. 4,374,829 mentioned above, with N-(1-ethoxycarbonyl-3-phenylpropyl)-L-alanyl-L-proline, that is, enalapril, being preferred, any of the phosphonate substituted amino or imino acids or salts disclosed in U.S. Pat. No. 4,452,790 with (S)-1-[6-amino-2-[[hydroxy-(4-phenylbutyl)phosphinyl]oxy]-1-oxohexyl]-L-proline or (ceronapril) being preferred, phosphinylalkanoyl prolines disclosed in U.S. Pat. No. 4,168,267 mentioned above with fosinopril being preferred, any of the phosphinylalkanoyl substituted prolines disclosed in U.S. Pat. No. 4,337,201, and the phosphonamidates disclosed in U.S. Pat. No. 4,432,971 discussed above.

Other examples of ACE inhibitors that may be employed herein include Beecham's BRL 36,378 as disclosed in European Patent Application Nos. 80822 and 60668; Chugai's MC-838 disclosed in C.A. 102:72588v and *Jap. J. Pharmacol.* 40:373 (1986); Ciba-Geigy's CGS 14824 (3-([1-ethoxycarbonyl-3-phenyl-(1S)-propyl]amino)-2,3,4,5-tetrahydro-2-oxo-1-(3S)-benzazepine-1 acetic acid HCl) disclosed in U.K. Patent No. 2103614 and CGS 16,617 (3(S)-[[(1S)-5-amino-1-carboxypentyl]amino]-2,3,4,5-tetrahydro-2-oxo-1H-1-benzazepine-1-ethanoic acid) disclosed in U.S. Pat. No. 4,473,575; cetapril (alacepril, Dainippon) disclosed in Eur. Therap. Res. 39:671 (1986); 40:543 (1986); ramipril (Hoechsst) disclosed in Euro. Patent No. 79-022 and *Curr. Ther. Res.* 40:74 (1986); Ru 44570 (Hoechst) disclosed in *Arzneimittelforschung* 34:1254 (1985), cilazapril (Hoffman-LaRoche) disclosed in *J. Cardiovasc. Pharmacol.* 9:39 (1987); R 31-2201 (Hoffman-LaRoche) disclosed in *FEBS Lett.* 165:201 (1984); lisinopril (Merck), indalapril (delapril) disclosed in U.S. Pat. No. 4,385,051; indolapril (Schering) disclosed in *J. Cardiovasc. Pharmacol.* 5:643, 655 (1983), spirapril (Schering) disclosed in *Acta. Phannacol. Toxicol.* 59 (Supp. 5): 173 (1986); perindopril (Servier) disclosed in *Eur. J. clin. Phannacol.* 31:519 (1987); quinapril (Warner-Lambert) disclosed in U.S. Pat. No. 4,344,949 and CI925 (Warner-Lambert) ([3S-[2[R(*)R(*)]]3R(*)]-2-[2-[[1-(ethoxy-carbonyl)-3-phenylpropyl]amino]-1-oxopropyl]-1,2,3,4-tetrahydro-6,7-dimethoxy-3-isoquinolinecarboxylic acid HCl)disclosed in *Pharmacologist* 26:243, 266 (1984), WY-44221 (Wyeth) disclosed in *J. Med. Chem.* 26:394 (1983).

Preferred ACE inhibitors are captopril, fosinopril, enalapril, lisinopril, quinapril, benazepril, fentiapril, ramipril and moexipril.

NEP/ACE inhibitors may also be employed herein in that they possess neutral endopeptidase (NEP) inhibitory activity and angiotensin converting enzyme (ACE) inhibitory activity. Examples of NEP/ACE inhibitors suitable for use herein include those disclosed in U.S. Pat. Nos. 5,362,727, 5,366,973, 5,225,401, 4,722,810, 5,223,516, 4,749,688, U.S. Pat. No. 5,552,397, U.S. Pat. No. 5,504,080, U.S. Pat. No. 5,612,359, U.S. Pat. No. 5,525,723, European Patent Application 0599,444, 0481,522, 0599,444, 0595,610, European Patent Application 0534363A2, 534,396 and 534,492, and European Patent Application 0629627A2.

Preferred are those NEP/ACE inhibitors and dosages thereof which are designated as preferred in the above patents/applications which U.S. patents are incorporated herein by reference; most preferred are omapatrilat, BMS 189,921 ([S-(R*,R*)]-hexahydro-6-[(2-mercapto-1-oxo-3-phenylpropyl)amino]-2,2-dimethyl-7-oxo-1H-azepine-1-acetic acid (gemopatrilat)) and CGS 30440.

The angiotensin II receptor antagonist (also referred to herein as angiotensin II antagonist or AII antagonist) suitable for use herein includes, but is not limited to, irbesartan, losartan, valsartan, candesartan, telmisartan, tasosartan or eprosartan, with irbesartan, losartan or valsartan being preferred.

A preferred oral dosage form, such as tablets or capsules, will contain the ACE inhibitor or AII antagonist in an amount within the range from abut 0.1 to about 500 mg, preferably from about 5 to about 200 mg and more preferably from about 10 to about 150 mg.

For parenteral administration, the ACE inhibitor, angiotensin II antagonist or NEP/ACE inhibitor will be employed in an amount within the range from about 0.005 mg/kg to about 10 mg/kg and preferably from about 0.01 mg/kg to about 1 mg/kg.

Where a drug is to be administered intravenously, it will be formulated in conventional vehicles, such as distilled water, saline, Ringer's solution or other conventional carriers.

It will be appreciated that preferred dosages of ACE inhibitor and AII antagonist as well as other antihypertensives disclosed herein will be as set out in the latest edition of the Physician's Desk Reference (PDR).

Other examples of preferred antihypertensive agents suitable for use herein include omapatrilat (Vanlev®) amlodipine besylate (Norvasc®), prazosin HCl (Minipress®), verapamil, nifedipine, nadolol, diltiazem, felodipine, nisoldipine, isradipine, nicardipine, atenolol, carvedilol, sotalol, terazosin, doxazosin, propranolol, and clonidine HCl (Catapres®).

Diuretics which may be employed in combination with compounds of formula I include hydrochlorothiazide, torasemide, furosemide, spironolactono, and indapamide.

Antiplatelet agents which may be employed in combination with compounds of formula I of the invention include aspirin, clopidogrel, ticlopidine, dipyridamole, abciximab, tirofiban, eptifibatide, anagrelide, and ifetroban, with clopidogrel and aspirin being preferred.

The antiplatelet drugs may be employed in amounts as indicated in the PDR. Ifetroban may be employed in amounts as set out in U.S. Pat. No. 5,100,889.

Antiosteoporosis agents suitable for use herein in combination with the compounds of formula I of the invention include parathyroid hormone or bisphosphonates, such as MK-217 (alendronate) (Fosamax®).

Dosages employed for the above drugs will be as set out in the Physician's Desk Reference.

Pharmaceutical Formulations

The pharmaceutical composition of the invention includes a pharmaceutically acceptable carrier, adjuvant or vehicle that may be administered to a subject, together with a compound of the present invention, and which does not destroy the pharmacological activity thereof. Pharmaceutically acceptable carriers, adjuvants and vehicles that may be used in the pharmaceutical compositions of the present invention include, but are not limited to, the following: ion exchangers, alumina, aluminum stearate, lecithin, self-emulsifying drug delivery systems ("SEDDS") such as d-(tocopherol polyethyleneglycol 1000 succinate), surfactants used in pharmaceutical dosage forms such as Tweens or other similar polymeric delivery matrices, serum proteins such as human serum albumin, buffer substances such as phosphates, glycine, sorbic acid, potassium sorbate, partial glyceride mixtures of saturated vegetable fatty acids, water, salts or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β- and γ-cyclodextrin, or chemically modified derivatives such as hydroxyalkylcyclodextrins, including 2-and 3-hydroxypropyl-β-cyclodextrins, or other solubilized derivatives may also be used to enhance delivery of the modulators of the present invention.

The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The compounds of the invention may be administered by any suitable means, for example, orally, such as in the form of tablets, capsules, granules or powders; sublingually; buccally; parenterally, such as by subcutaneous, intravenous, intramuscular, or intrastemal injection or infusion techniques (e.g., as sterile injectable aqueous or non-aqueous solutions or suspensions); nasally such as by inhalation spray; topically, such as in the form of a cream or ointment; or rectally such as in the form of suppositories; in dosage unit formulations containing non-toxic, pharmaceutically acceptable vehicles or diluents. The compounds of the invention may, for example, be administered in a form suitable for immediate release or extended release. Immediate release or extended release may be achieved by the use of suitable pharmaceutical compositions including the compounds of the invention, or, particularly in the case of extended release, by the use of devices such as subcutaneous implants or osmotic pumps. The compounds of the invention may also be administered liposomally.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The present compunds may also be delivered through the oral cavity by sublingual and/or buccal administration. Molded tablets, compressed tablets or freeze-dried tablets are exemplary forms which may be used. Exemplary compositions include those formulating the compound(s) of the invention with fast dissolving diluents such as mannitol, lactose, sucrose and/or cyclodextrins. Also included in such formulations may be high molecular weight excipients such as celluloses (Avicel) or polyethylene glycols (PEG). Such formulations may also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions in saline which may contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid. The term "parenteral" as used herein includes subcutaneous, intracutaneous, intravenous, intramuscular, intraarticular, intraarterial, intrasynovial, intrasternal, intrathecal, intralesional and intracranial injection or infusion techniques.

Exemplary compositions for rectal administration include suppositories which may contain, for example, a suitable non-irritating excipient, such as cocoa butter, synthetic glyceride esters or polyethylene glycols, which are solid at ordinary temperatures, but liquify and/or dissolve in the rectal cavity to release the drug.

Exemplary compositions for topical administration include a topical carrier such as Plastibase (mineral oil gelled with polyethylene).

The effective amount of a compound of the present invention may be determined by one of ordinary skill in the art, and includes exemplary dosage amounts for an adult human of from about 0.1 to 500 mg/kg of body weight of active compound per day, or between 5 and 2000 mg per day which may be administered in a single dose or in the form of individual divided doses, such as from 1 to 5 times per day. It will be understood that the specific dose level and frequency of dosage for any particular subject may be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like.

A typical capsule for oral administration contains compounds of structure I (250 mg), lactose (75 mg) and magnesium stearate (15 mg). The mixture is passed through a 60 mesh sieve and packed into a No. 1 gelatin capsule.

A typical injectable preparation is produced by aseptically placing 250 mg of compounds of structure I into a vial, aseptically freeze-drying and sealing. For use, the contents of the vial are mixed with 2 mL of physiological saline, to produce an injectable preparation.

The compounds of formula I of the invention are glucocorticoid receptor modulators as shown either by their ability to bind glucocorticoid receptors in GR binding assays, or by their ability to inhibit AP-1 activity as indicated in cellular transrepressional assays, and cause none to minimal transactivation as indicated in cellular transscriptional assays.

Compounds of the invention, including the compounds described in the examples hereof, have been tested in at least one of the assay(s) described below and have glucocorticoid receptor (GR)/Dexamethasone (Dex) inhibition activity (>95% at 10 µM) and/or AP-1 inhibition activity ($EC_{50}$ at less than 15 µM).

Identical and/or similar assays are described in copending provisional application No. 60/396,907, filed Jul. 18, 2002 which is incorporated in its entireity herein by reference.

GR (Dex) Binding Assay

In order to measure the binding of compounds to Site I on the glucocorticoid receptor a commercially available kit was used (Glucocorticoid receptor competitor assay kit, Panvera Co., Madison, Wis.). Briefly, a cell lysate containing recombinantly expressed human full-length glucocorticoid receptor was mixed with a fluorescently labeled glucocorticoid (4 nM FITC-dexamethasone) plus or minus test molecule. After one hour at room temperature, the fluorescence polarization (FP) of the samples were measured. The FP of a mixture of receptor, fluorescent probe (i.e. FITC-dexamethasone) and 1 mM dexamethasone represented background fluorescence or 100% inhibition, whereas, the FP of the mixture without dexamethasone was taken to be 100% binding. The percentage inhibition of test molecules were then compared to the sample with 1 mM dexamethasone and expressed as % relative binding activity with dexamethasone being 100% and no inhibition is 0%. Test molecules were analyzed in the concentration range from 0.1 nM to 40 µM.

Site I binding assays for any NHR (Nuclear Hormone Receptor) are conducted similarly to the above. An appropriate cell lysate or purified NHR is used as the source of the NHR. The fluorescent probe and unlabeled competitor are appropriate for the specific NHR, i.e. are ligands for the specific NHR.

Cellular Transrepressional Assay

To measure the ability of test molecules to inhibit AP-1 induced transcriptional activity we utilized an A549 cell which was stably transfected with a plasmid containing 7× AP-1 DNA binding sites (pAP-1-Luc plasmid, Stratagene Co. La Jolla, Calif.) followed by the gene for luciferase. Cells were activated with 10 ng/ml of phorbol myristic acid (PMA) plus or minus test molecules for 7 hours. After 7 hours a luciferase reagent was added to measure luciferase enzymatic activity in the cell. After a 10 minute incubation of luciferase reagent with cells, luminescence was measured in a TopCount luminescence counter. Repression of AP-1 activity was calculated as the percentage decrease in the signal induced by PMA alone. Test molecules were analyzed in the concentration range from 0.1 nM to 40 µM. EC50s were determined by using standard curve fitting methods such as Excel fit (Microsoft Co.). An EC50 is the test molecule concentration at which there is a 50% repression of the maximal inhibition of transcription, i.e. a 50% reduction of AP-1 activity.

Other reporters and cell lines also may be used in a cellular transrepressional assay. A similar assay is performed in which NF-κB activity is measured. A plasmid containing NF-κB DNA binding sites is used, such as pNF-kB-Luc, (Stratagene, La Jolla Calif.), and PMA or another stimulus, such as TNF-α or lipopolysaccharide, is used to activate the NF-κB pathway. NF-κB assays similar to that described in Yamamoto K., et al., *J Biol Chem* December 29; 270(52): 31315-20 (1995) may be used.

The cellular transrepressional assays described above may be used to measure transrepression by any NHR. One of skill in the art will understand that assays may require the addition of components, such as a stimulus (eg. PMA, lipopolysaccharide, TNF-α, etc) which will induce transcription mediated by AP-1 or NF-κB. Additionally, AR mediated transrepression may be measured by the assay described in Palvimo J J, et al. *J Biol Chem* September 27; 271(39):24151-6 (1996), and PR mediated transrepression may be measured by the assay described in Kalkhoven E., et al. *J Biol Chem* March 15; 271(11):6217-24 (1996).

The following abbreviations are employed in the following Preparations and Examples:
Ph=phenyl
Bn=benzyl
t-Bu=tertiary butyl
Me=methyl
Et=ethyl
TMS=trimethylsilyl
$TMSN_3$=trimethylsilyl azide
TBS=tert-butyldimethylsilyl
FMOC=fluorenylmethoxycarbonyl
Boc=tert-butoxycarbonyl
Cbz=carbobenzyloxy or carbobenzoxy or benzyloxycarbonyl
THF=tetrahydrofuran
$Et_2O$=diethyl ether
hex=hexanes
EtOAc=ethyl acetate
DMF=dimethyl formamide
MeOH=methanol
EtOH=ethanol
i-PrOH=isopropanol
DMSO=dimethyl sulfoxide
DME=1,2 dimethoxyethane
DCE=1,2 dichloroethane
HMPA=hexamethyl phosphoric triamide
HOAc or AcOH=acetic acid
TFA=trifluoroacetic acid
TFAA=trifluoroacetic anhydride
i-$Pr_2$NEt=diisopropylethylamine
$Et_3$N=triethylamine
NMM=N-methyl morpholine DMAP=4-dimethylaminopyridine
NaBH₄=sodium borohydride
NaBH(OAc)₃=sodium triacetoxyborohydride
DIBALH=diisobutyl aluminum hydride
LAH or LiAlH₄=lithium aluminum hydride
n-BuLi=n-butyllithium
LDA=lithium diisopropylamide
Pd/C=palladium on carbon
PtO₂=platinum oxide
KOH=potassium hydroxide
NaOH=sodium hydroxide
LiOH=lithium hydroxide
K₂CO₃=potassium carbonate
NaHCO₃=sodium bicarbonate
DBU=1,8-diazabicyclo[5.4.0]undec-7-ene
EDC (or EDC.HCl) or EDCI (or EDCI.HCl) or EDAC=3-ethyl-3'-(dimethylamino)propyl-carbodiimide hydrochloride (or 1-(3-dimethylaminopropyl)-3-ethylcarbodiimide hydrochloride)
HOBT or HOBT.H₂O=1-hydroxybenzotriazole hydrate
HOAT=1-Hydroxy-7-azabenzotriazole
BOP reagent=benzotriazol-1-yloxy-tris (dimethylamino) phosphonium hexafluorophosphate
NaN(TMS)₂=sodium hexamethyldisilazide or sodium bis (trimethylsilyl)amide
Ph₃P=triphenylphosphine
Pd(OAc)₂=Palladium acetate
(Ph₃P)₄Pd°=tetrakis triphenylphosphine palladium
DEAD=diethyl azodicarboxylate
DIAD=diisopropyl azodicarboxylate
Cbz-Cl=benzyl chloroformate
CAN=ceric ammonium nitrate
SAX=Strong Anion Exchanger
SCX=Strong Cation Exchanger
Ar=argon
N₂=nitrogen
min=minute(s)
h or hr=hour(s)
L=liter
mL=milliliter
μL=microliter
g=gram(s)
mg=milligram(s)
mol=moles
mmol=millimole(s)
meq=milliequivalent
RT=room temperature
sat or sat'd=saturated
aq.=aqueous
TLC=thin layer chromatography
HPLC=high performance liquid chromatography
LC/MS=high performance liquid chromatography/mass spectrometry
MS or Mass Spec=mass spectrometry
NMR=nuclear magnetic resonance
NMR spectral data: s=singlet; d=doublet; m=multiplet; br=broad; t=triplet
mp=melting point Preparations The preparations set out below are for the synthesis of reagents that were not obtained from commercial sources and were employed for the preparation of compounds of formula I of the invention. All chemical structures in the tables and schemes are racemic unless specified otherwise.

Preparation 1

2-Amino-4-[1-(4-fluoro)naphthyl]thiazole 1a

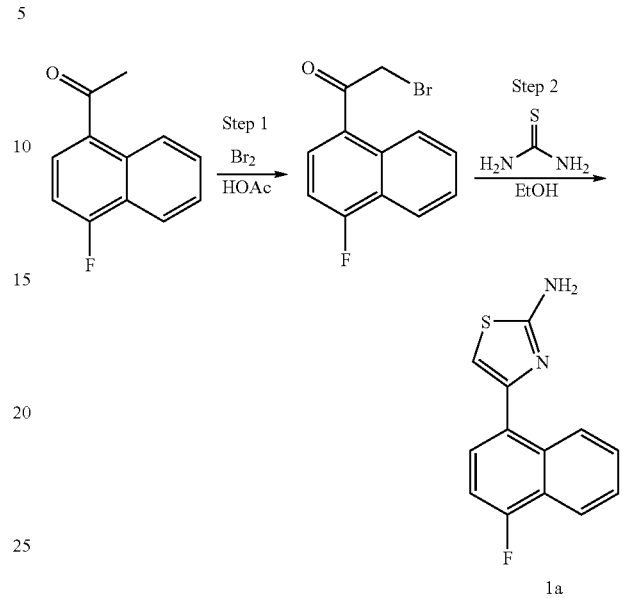

Step 1

To a solution of 4'-fluoro-1'-acetonaphthone (28.69 mmol, 5.4 g) in 1,4-dioxane (18.0 mL) at 0° C. was added bromine (35.13 mmol, 5.61 g). After 3 hours at room temperature the reaction mixture was concentrated in vacuo to give 7.66 g (100% yield) of the product of step 1.

Step 2

To a solution of the product of step 1 (28.69 mmol, 7.66 g) in ethyl alcohol (20 mL) at room temperature was added thiourea (36.13 mmol, 2.75 g). After 1 hour at room temperature a precipitate formed. To the reaction mixture was added water (100 mL) and the solid was collected by vacuum filtration. The solid was then washed with water (3×100 mL) and dichloromethane (3×100 mL). The solid was then dried in vacuo to give 5.5 g (Y: 75%) of the title compound 1a. MS (E+) m/z: 245 (MH⁺).

In a similar manner the following compounds were prepared from the corresponding α-bromo-ketone.

| Preparation | Structure |
|---|---|
| 1b | 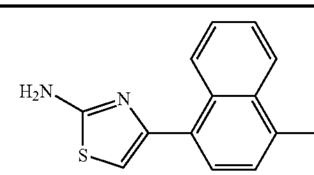 |
| 1c | 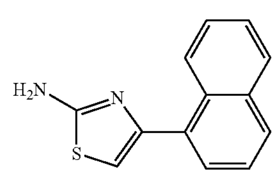 |

-continued

| Preparation | Structure |
|---|---|
| 1d | 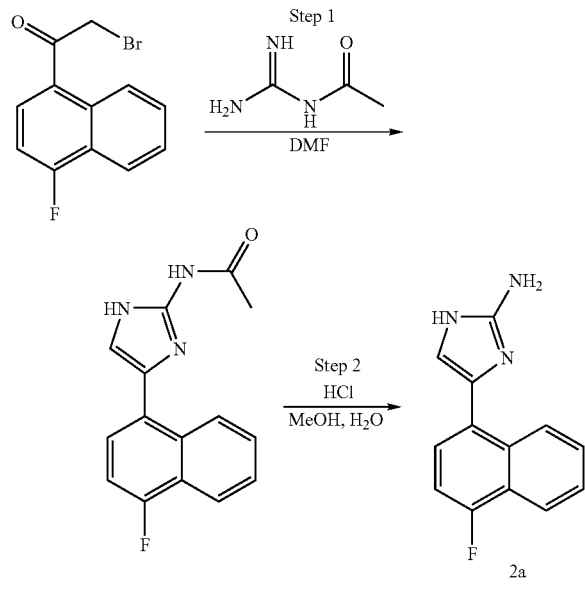 |
| 1e | 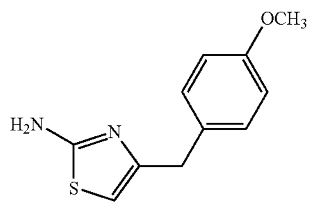 |

Preparation 2

2-Amino-4-[1-(4-fluoro)naphthyl]imidazole 2a

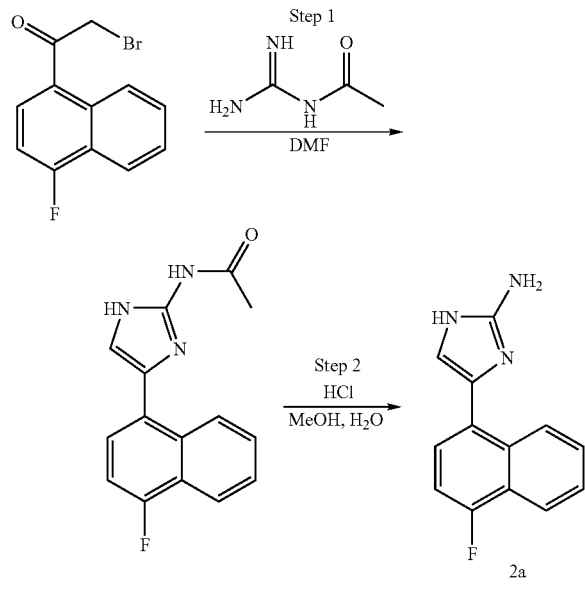

Step 1

To a solution of the product of preparation 1a, step 1 (18.73 mmol, 5.0 g) in DMF (15 mL) at room temperature was added 1-acetylguanidine (57.43 mmol, 5.80 g). After 5 hours at room temperature, the reaction mixture was diluted with water (100 mL) and extracted with ethyl acetate (3×100 mL). The organic phases were concentrated in vacuo and the residue chromatographed on silica gel (eluted with 5% methanol in dichloromethane) to give 2.0 g (39% yield) of the product of step 1. MS (E+) m/z: 270 (MH+).

Step 2

To a solution of the product of step 1 (7.43 mmol, 2.0 g) in methanol (17 mL) was added water (8.5 mL) and 12 N HCl (12.0 mL). After 1 hour at reflux the reaction mixture was concentrated in vacuo to approximately 15 mL. The resulting solution was then purified and neutralized by cation exchange SPE to give 1.66 g (99% yield) of the title compound 2a. MS (E+) m/z: 228 (MH+).

In a similar manner the following compounds were prepared from the corresponding α-bromo-ketone.

| Preparation | Structure |
|---|---|
| 2b | 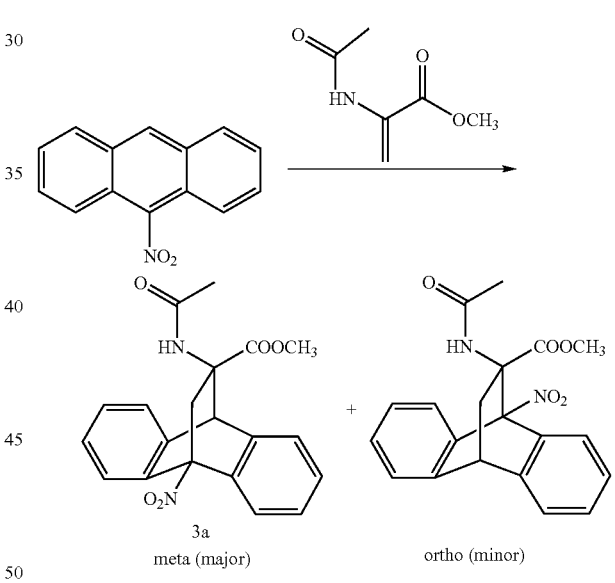 |
| 2c | 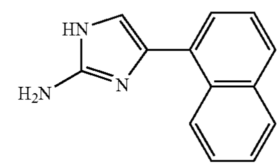 |

Preparation 3

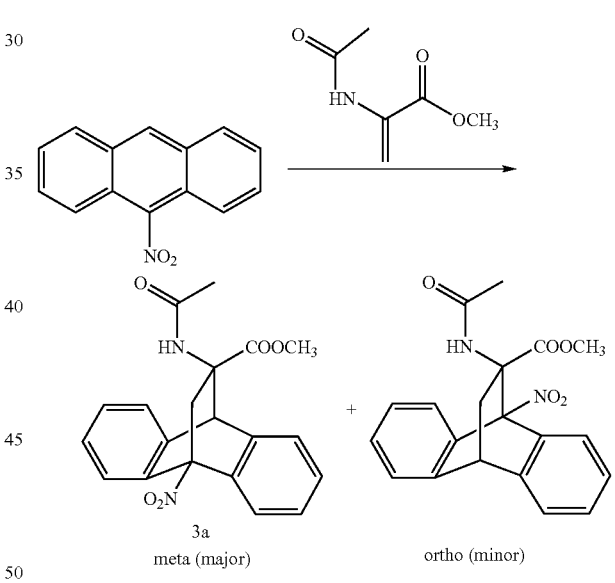

To a solution of 9-nitroanthracene (1.5 g, 6.73 mmol) in nitrobenzene (10 ml) was added methyl 2-acetamido-acrylate (1.5 g, 10.1 mmol, 1.5 equiv.) and hydroquinone (165 mg, 1.0 mmol, 0.15 mmol). The reaction mixture was heated at 166° C. for 48 hours to afford the crude product 3a (meta:ortho=>99:1). The crude product was purified via flash chromatography on silica gel with 20%, 40% ethyl acetate in hexane as eluents to remove nitrobenzene. Elution with 1%, 3% and 10% MeOH in dichloromethane afforded the product of 3a as a white solid (1.472 g, 4.02 mmol, 60% yield). LC/MS m/z 367.16 (M+H)+); HPLC (Column: Shimadzu VP-ODS, C-18 Ballistic; 10-90% aq CH3OH/0.1% H3PO4, same for other compounds unless noted) Rt: 3.113 min. 100% purity.

Alternatively, the Diels-Alder reaction can be carried out under the microwave irradiation. A solution of 9-nitroanthracene (100 mg, 0.448 mmol), methyl 2-acetamido-acrylate (321 mg, 2.24 mmol. 5 equiv.) and hydroquinone (4.93 mg, 0.1 equiv.) in DMF (1 ml) was subjected to microwave irradiation at 200° C. for 1 hour. After cooling, an aliquot of the reaction mixture was assayed by HPLC, indicating a 28% conversion of the starting anthracene to the meta product 3a. Several batches of the crude product mixture were combined and directly purified via prep HPLC (column: YMC, C-18 Ballistic, 30×1.00 mm; 10-90% aq $CH_3OH$/0.1% TFA, 0.25 mL/min. flow rate, 220 nm detection wavelength) to give the pure product of meta isomer 3a as a white solid.

In a similar manner, the following compounds were prepared from methyl 2-acetamido-acrylate and the appropriate anthracene.

| Preparation Number | Structure |
|---|---|
| 3b | 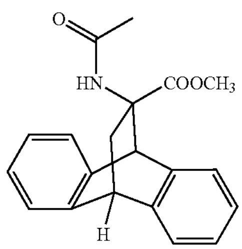 |
| 3c | 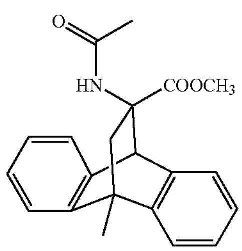 |
| 3d | 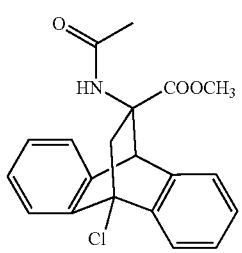 |

Preparaton 4

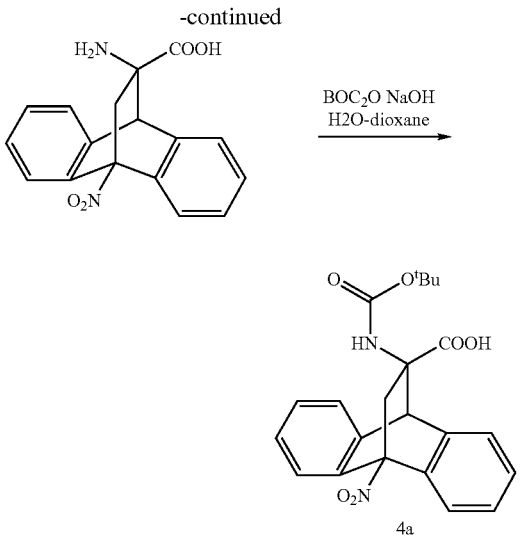

To a solution of the product of 3a in Preparation 3 (564 mg, 1.54 mmom) in dioxane (8 ml) was added concentrated hydrochloride acid (18 ml). The reaction mixture was refluxed for 42 hours. After removal of solvents, the crude product was suspended in dichloromethane and filtered to provide the amino acid (595 mg, 91% yield). LC/MS ES⁻ m/z 309.1 (M−1); HPLC Rt: 2.213 min. 99% purity.

The amino acid (489 mg, 1.34 mmol) was dissolved in dioxane (7 ml). The resulting solution was adjusted to pH 12 with 1N aqueous NaOH, and to this solution was added di-t-butyl dicarbonate (1.17 g, 5.35 mmol). The reaction mixture was stirred at room temperature for 48 hours and gradually formed a white precipitate. After filtration to remove the white precipitate, the filtrate was concentrated. The residue was taken into 1N hydrochloride acid and ethyl acetate. After separation, the organic layer was washed with brine, dried over magnesium sulfate and concentrated in vacuo to afford the product of 4a as a white solid (547.4 mg, 99% yield). LC/MS ES⁻ m/z 409.1 (M−1); HPLC Rt: 3.573 min. 100% purity.

In a similar manner, the following compounds were prepared from the appropriate products 3b to 3d of Preparation 3.

| Preparation Number | Structure |
|---|---|
| 4b | 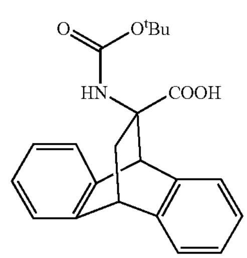 |

| Preparation Number | Structure |
|---|---|
| 4c | 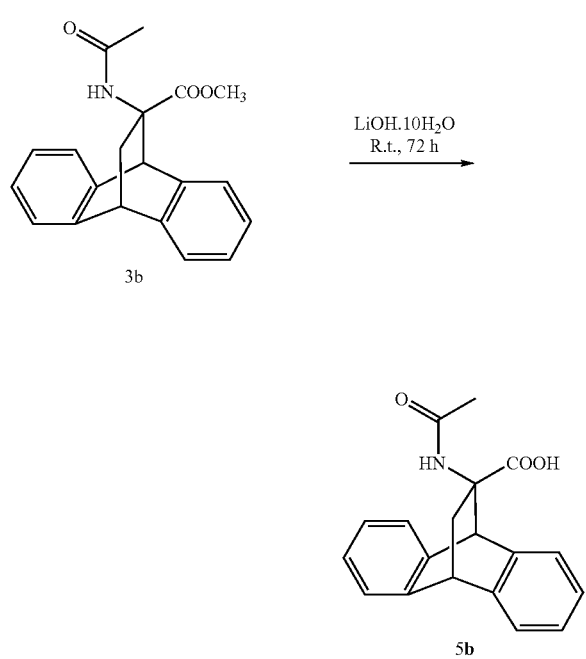 |
| 4d | 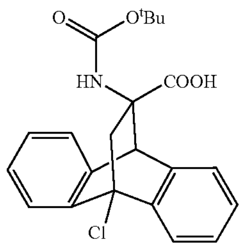 |

Preparation 5

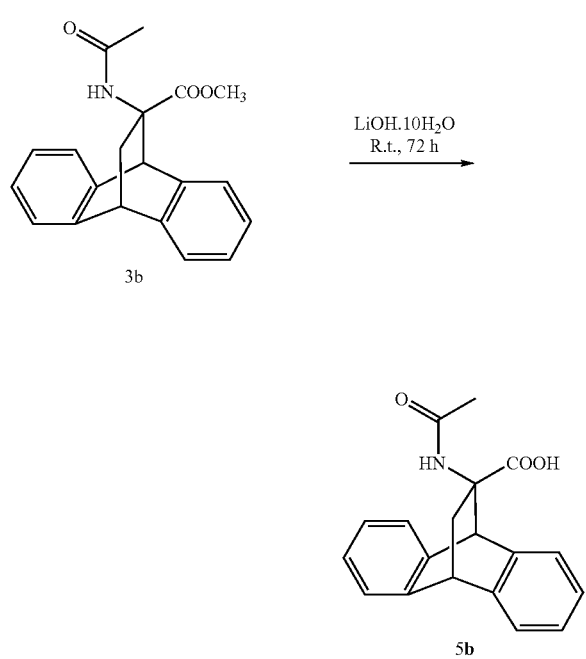

To a solution of the product of 3b (70 mg, 0.218 mmol) in THF (1.5 ml) was added an aqueous solution of lithium hydroxide (1.5 ml water). The reaction mixture was stirred at room temperature for 7 days. After removal of solvent, the crude product was taken into water and ethyl acetate. The aqueous layer was acidified with 1N hydrochloride acid, and extracted with ethyl acetate. The extract was washed with brine, dried over magnesium sulfate, and concentrated to afford the title compound of 5b as a white solid, (57 mg, 0.186 mmol, 85.2% yield). LC/MS m/z 308.02 (M+H)+; HPLC Rt: 2.84 min. 97% purity.

Preparation 6

4-(4-Pyridin-4-yl-benzyl)-1H-imidazol-2-ylamine 6

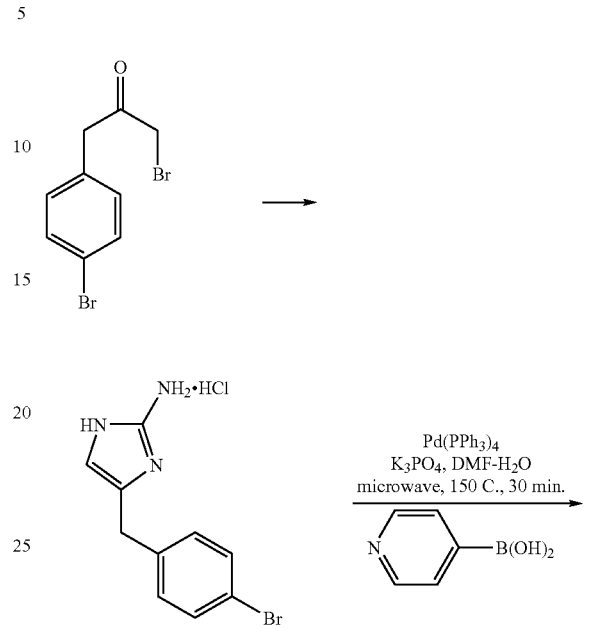

4-(4-Bromobenzyl)-1H-imidazol-2-amine hydrochloride (200 mg, 0.795 mmol), prepared from 1-bromo-3-(4-bromophenyl)-propan-2-one using the procedure similar to that described in Preparation 2, was dissolved in DMF (3 ml). To this solution were added pyridine-4-yl boronic acid (245 mg, 1.99 mmol) and 2 ml of a 2M aqueous solution of potassium phosphate ($K_3PO_4$). The resulting solution was purged through with nitrogen for 15 minutes, after which tetrakis (triphenylphosphine)-palladium (95 mg, 0.08 mmol) was added. The solution was purged with nitrogen for an additional 5 minutes, and then was subjected to microwave irradiation at 150° C. for 30 minutes. The crude product was purified via preparative HPLC (column: YMC, C-18 Ballistic, 30×100 mm; 10-90% aq CH3OH/0.1% TFA, 0.25 mL/min. flow rate, 220 nm detection wavelength) to give the product as a trifluoroacetic acid salt (119 mg, 36% yield), which was neutralized by cation exchange SPE to provide the title compound of 6 as a white solid. LC/MS m/z 251.16 (M+H)+; HPLC Rt: 0.568 min.

4-(4-Pyridin-4-yl-benzyl)-thiazol-2-ylamine 7

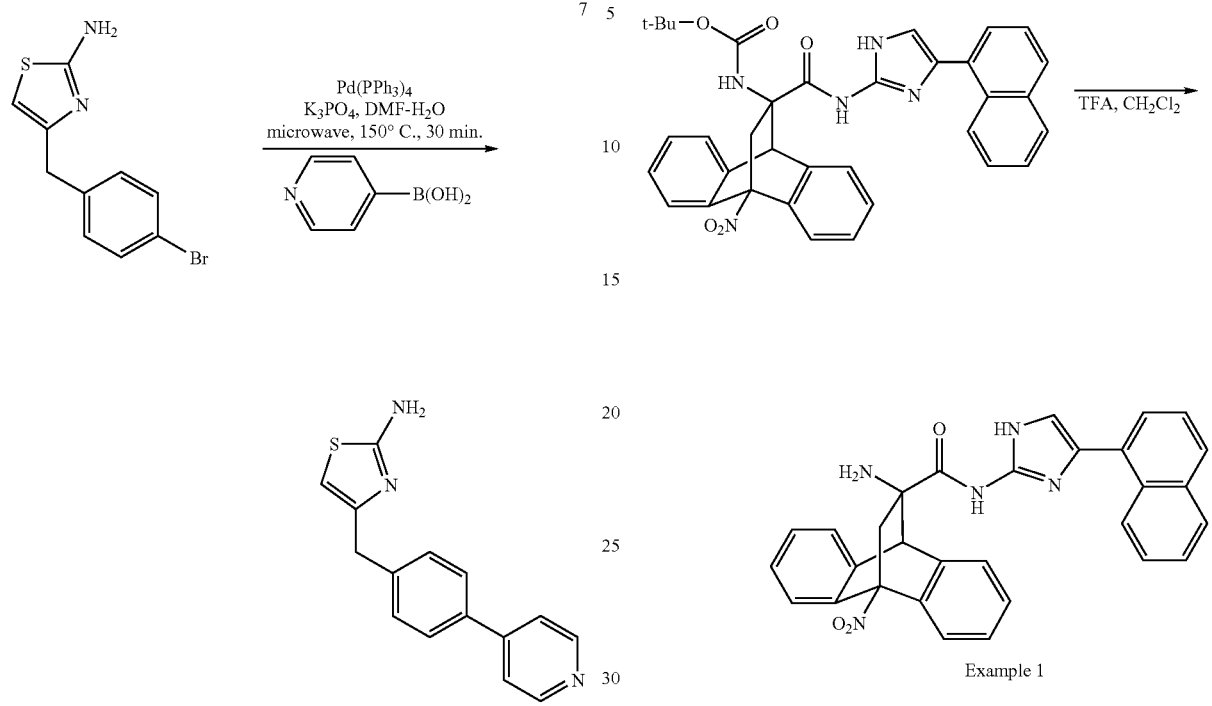

In a similar manner to Preparation 6, step 3, the Suzuki coupling reaction of pyridine-4-yl boronic acid and 4-(4-bromo-benzyl)-thiazol-2-ylamine, was prepared via reaction of 1-bromo-3-(4-bromo-phenyl)-propan-2-one and thiourea in ethyl alcohol according to the procedure described in Preparation 1, step 2, gave the title compound 7. LC/MS m/z 268.08 (M+H)+; HPLC Rt: 0.598 min.

The following Examples illustrate embodiments of the inventive compounds and starting materials, and are not intended to limit the scope of the claims.

EXAMPLE 1

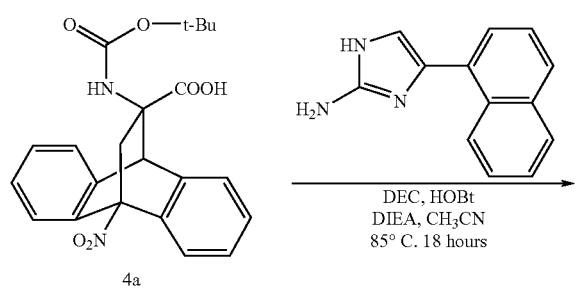

To a solution of the title compound of 4a (56 mg, 0.136 mmol) of Preparation 4 in acetonitrile (1.5 mL) were added 1-[3-(dimethylamino)propyl]-3-ethylcarbodiimide hydrochloride (EDC) (40 mg, 0.2 mmol), 1-hydroxy-benzotriazole (HOBt) (28 mg. 0.2 mmol), diisopropylethyl amine (0.025 mL, 0.18 mmol, 2.5 equi.), and 2-amino-4-naphthylimidazole (53 mg, 0.25 mmol). The reaction solution was heated at 85° C. for 18 hours. After removal of solvent, the crude product was purified by HPLC chromatography to yield the coupling product (38.6 mg, 0.77 mmol, 56.6% yield). This product was dissolved in dichloromethane (2 ml), and cooled to 0° C. Triflurroacetic acid (0.8 ml) was added. The reaction mixture was allowed to warm to room temperature overnight. After removal of the solvent, the obtained TFA salt of the amine was purified and neutralized by cation exchange SPE with 2M ammonia in MeOH to afford the title compound of Example 1 as a white solid (19 mg, 0.038 mmol, 59.2% yield). LC/MS m/z 502.40 (M+H)+; HPLC Rt: 3.063 min. 98% purity.

EXAMPLES 2 TO 25

In a similar manner to Example 1, Examples 2-25 were prepared via the coupling reaction of the appropriate acids (Preparations 3b to 3d) and amines (Preparations 1, 2, 6 and 7).

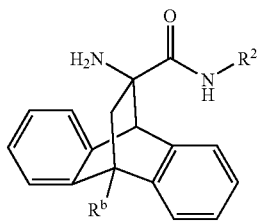
| Example # | R<sup>b</sup> | R² | HPLC Rt: minute | MS [m/z (M+H)] |
|---|---|---|---|---|
| 2 | H | (thiazole-naphthyl-CH₃) | 3.39 | 488.09 |
| 3 | H | (imidazole-naphthyl-F) | 3.08 | 475.12 |
| 4 | NO₂ | (imidazole-phenyl-CH₃, F, vinyl) | 3.24 | 520.02 |
| 5 | H | (thiazole) | 2.10 | 348.29 |
| 6 | Cl | (thiazole-naphthyl-CH₃) | 3.51 | 522.22 |
| 7 | H | (thiazole-phenyl-C(O)NH-phenyl-OCH₃,Cl) | 3.31 | 607.28 |
| 8 | H | (thiazole-naphthyl) | 3.20 | 474.28 |

-continued
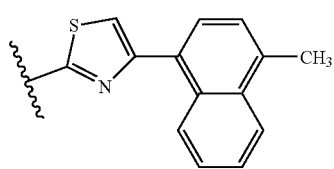
| Example # | $R^b$ | $R^2$ | HPLC Rt: minute | MS [m/z (M+H)] |
|---|---|---|---|---|
| 9 | $CH_3$ | 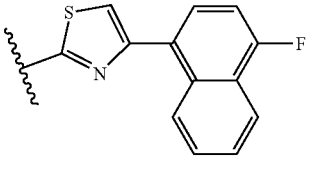 | 3.43 | 502.3 |
| 10 | $CH_3$ | 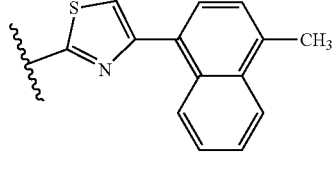 | 3.42 | 506.3 |
| 11 | $NO_2$ | 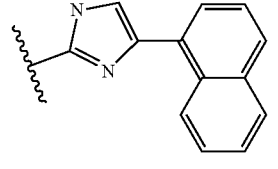 | 3.40 | 533.28 |
| 12 | $CH_3$ | 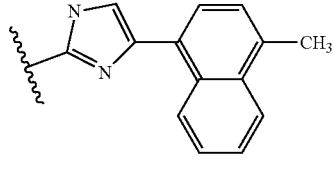 | 3.07 | 471.28 |
| 13 | $CH_3$ | 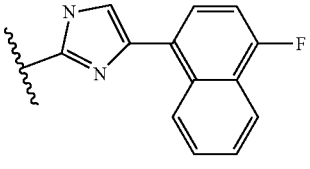 | 3.22 | 485.3 |
| 14 | Cl | 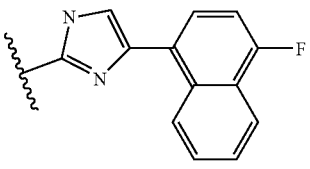 | 3.32 | 509.2 |
| 15 | $CH_3$ | | 3.18 | 489.24 |

-continued
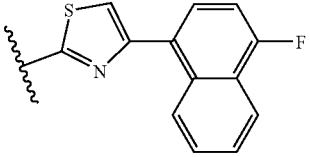
| Example # | R<sup>b</sup> | R² | HPLC Rt: minute | MS [m/z (M+H)] |
|---|---|---|---|---|
| 16 | Cl | 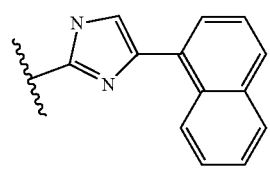 | 3.51 | 526.16 |
| 17 | Cl | 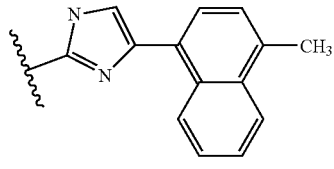 | 3.25 | 491.43 |
| 18 | Cl | 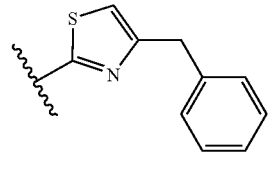 | 3.40 | 505.43 |
| 19 | NO₂ | 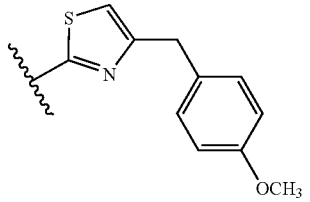 | 2.99 | 483.48 |
| 20 | NO₂ | 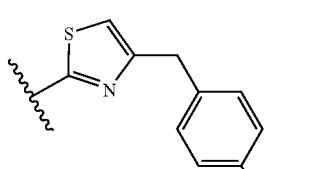 | 5.70 | 513.33 |
| 21 | Cl | 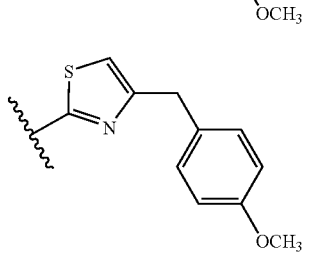 | 3.19 | 502.25 |
| 22 | CH₃ | | 3.09 | 482.31 |

-continued
| Example # | R^b | R^2 | HPLC Rt: minute | MS [m/z (M+H)] |
|---|---|---|---|---|
| 23 | $NO_2$ | (thiazole-CH2-phenyl-pyridyl) | 2.22 | 560.22 |
| 24 | Cl | (thiazole-CH2-phenyl-pyridyl) | 2.42 | 549.30 |
| 25 | $NO_2$ | (imidazole-CH2-phenyl-pyridyl) | 2.05 | 543.15 |
EXAMPLE 26
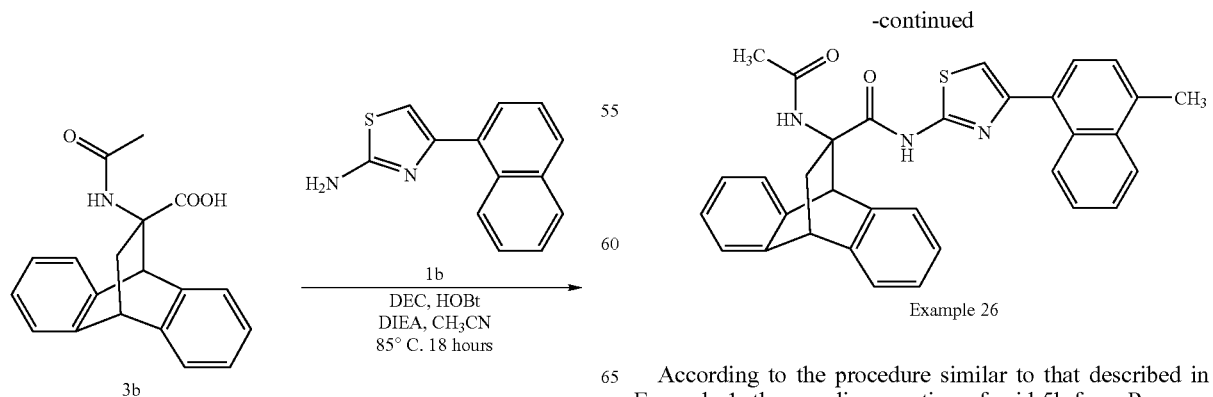
According to the procedure similar to that described in Example 1, the coupling reaction of acid 5b from Preparation 5 and 2-amino-4-[1-(4-methyl)naphthyl]thiazole 1b from Preparation 1 generated the title compound of Example 26. LC/MS m/z 530.07 (M+H)+; HPLC Rt: 4.09 min. 97% purity.

EXAMPLE 27

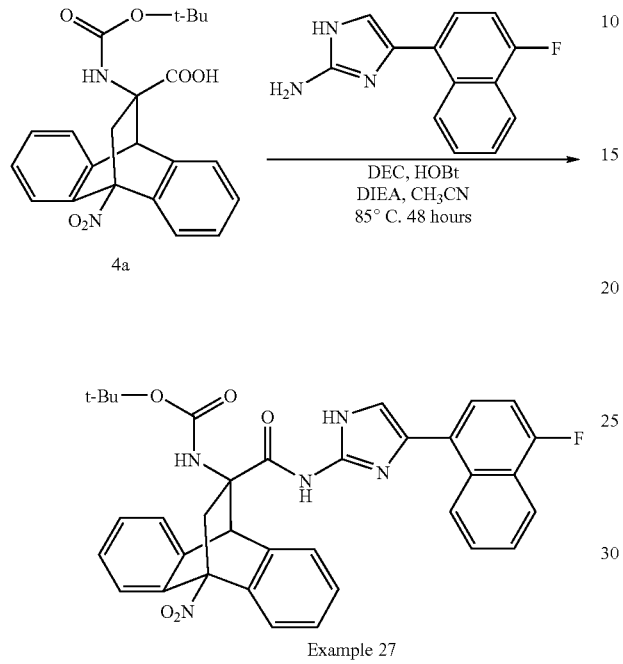

According to the procedure similar to that described for preparation of 6a in Example 1, the coupling reaction of acid 4a from Preparation 4 and 2-amino-4-[1-(4-fluoro)naphthyl]imidazole 2a from Preparation 2 generated the title compound of Example 27. LC/MS m/z 620.03 (M+H)⁺; HPLC Rt: 3.79 min. 100% purity.

EXAMPLE 28

In a similar manner to Example 27, Example 28 was prepared via the coupling reaction of acid 4d and 4-(4-pyridin-4-yl-benzyl)-thiazol-2-ylamine 7. HPLC Rt.: 3.61 minutes, MS (M+H): 649.27.

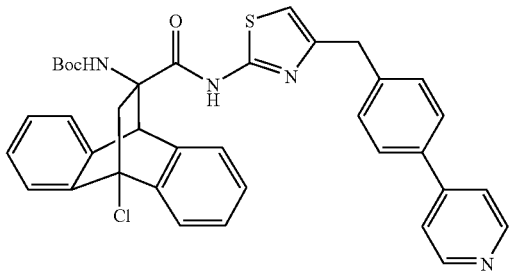

What is claimed is:
1. A compound having below structure of formula (I)

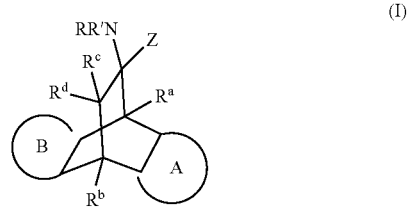

its stereoisomers thereof, or a pharmaceutically acceptable salt thereof, wherein R is hydrogen, alkyl, alkenyl, alkynyl, cycloalkyl, cycloalkylalkyl, aryl, heteroaryl, heteroarylalkyl, cycloheteroalkyl, cycloalkenyl, monoalkylaminoalkyl, dialkylaminoalkyl, cycloheteroalkylalkyl, hydroxyaryl, aryloxyalkyl, alkoxyalkyl and hydroxyalkyl, $S(O)_tR_3$, or $C(O)_tR_3$ wherein $R^3$ is selected from hydrogen, alkyl, alkenyl, alkynyl, alkoxy, cycloalkyl, cycloalkylalkyl, aryl, heteroaryl, heteroarylalkyl, cycloheteroalkyl, cycloalkenyl, monoalkylaminoalkyl, dialkylaminoalkyl, cycloheteroalkylalkyl, hydroxyaryl, aryloxyalkyl, alkoxyalkyl and hydroxyalkyl;

R' is selected from hydrogen, alkyl, alkenyl, alkynyl, alkoxy, cycloalkyl, cycloalkylalkyl, aryl, heteroaryl, heteroarylalkyl, cycloheteroalkyl, cycloalkenyl, monoalkylaminoalkyl, dialkylaminoalkyl, cycloheteroalkylalkyl, hydroxyaryl, aryloxyalkyl, alkoxyalkyl and hydroxyalkyl;

$R^a$ and $R^b$ are independently selected from hydrogen, halogen, hydroxy, alkyl, alkenyl, alkynyl, alkoxy, aryl, aryloxy, heteroaryl, cycloheteroalkyl, heteroarylalkyl, cycloheteroalkylalkyl, cyano, heteroarylaminocarboyl, cycloheteroalkylcarbonyl, cyanoalkyl, alkylaminoalkyl, hydroxyalkyl, hydroxyaryl, aryloxyalkyl, alkoxyalkyl, nitro, $NR^eR^f$, CHO, $CO_2$alkyl, $CONR^eR^f$, $CH_2NR^eR^f$, $CO_2H$, $CH_2OH$, $CH_2NR^eR^f$, $NHCOR^g$, $NHCONR^eR^f$ and $NHSO_2R^g$;

$R^c$ and $R^d$ are independently selected from hydrogen, alkyl, alkenyl, alkynyl, alkoxy, $NR^eR^f$, aryl, hydroxy, aryloxy, heteroaryl, cycloheteroalkyl, heteroarylalkyl, cycloheteroalkylalkyl, hydroxyaryl, and aryloxyalkyl;

$R^e$ and $R^f$ at each occurrence are the same or different and are independently selected from hydrogen, aryl, alkyl, alkenyl, alkynyl, alkoxy, amino, substituted amino, alkoxyalkyl, alkylaminoalkyl, dialkylaminoalkyl, heteroaryl, cycloheteroalkyl, heteroarylalkyl, cycloheteroalkylalkyl, cycloalkyl, and cycloalkylalkyl, provided $R^e$ and $R^f$ are not both alkoxy or amino;

or $R^e$ and $R^f$ at each occurrence can be taken together with the nitrogen to which they are attached to form a 5-, 6-or 7-membered heteroaryl or cycloheteroalkyl ring which contains 1, 2 or 3 hetero atoms which can be N, O or S;

$R^g$ at each occurrence is selected from hydrogen, aryl, alkyl, alkenyl, alkynyl, alkoxy, amino, substituted amino, alkoxyalkyl, alkylaminoalkyl, dialkylaminoalkyl, heteroaryl, cycloheteroalkyl, heteroarylalkyl, cycloheteroalkylalkyl, cycloalkyl and cycloalkylalkyl;

Z is $S(O)_t'NR^1R^2$, $C(O)NR^1R^2$ or $CH_2NR^1R^2$ wherein $R^1$ and $R^2$ are the same or different and are independently selected from hydrogen, alkyl, alkenyl, alkynyl, alkoxy, cycloalkyl, cycloalkylalkyl, aryl, heteroaryl, heteroarylalkyl, cycloheteroalkyl, cycloalkenyl, monoalkylaminoalkyl, dialkylaminoalkyl, cycloheteroalkylalkyl, hydroxyaryl, aryloxyalkyl, alkoxyalkyl or hydroxyalkyl;
t is 1 or 2;
each occurrence of t, $R^e$, $R^f$, and $R^g$ are chosen independently;
the A ring represents a saturated, partially saturated or unsaturated 6-membered carbocyclic or heterocyclic ring, wherein the heterocyclic ring contains only one N atom; and
the B ring represents a saturated, partially saturated or unsaturated 6-membered carbocyclic or heterocyclic ring, wherein the heterocyclic ring contains only one N atom.

2. The compound as defined in claim 1, its stereoisomers thereof, or a pharmaceutically acceptable salt thereof, wherein the A ring has the structure

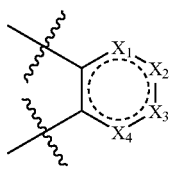

and the B ring has the structure

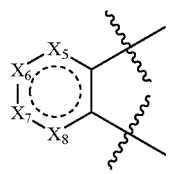

wherein:
$X_1$, $X_2$, $X_3$ and $X_4$, are the same or different and are independently selected from CH, $CH_2$, $CHR^4$, $CR^5$, $R^6$, N, NH, $NR^7$, O or S, and $X_5$, $X_6$, $X_7$ and $X_8$ are the same or different and are independently selected from CH, $CH_2$, $CHR^8$, $CR^9R^{10}$, N, NH, $NR^{11}$, O or S;
$R^4$, $R^5$, $R^6$, $R^8$, $R^9$, $R^{10}$ and $R^{12}$ are the same or different and are independently selected from hydrogen, halo, alkyl, aryl, cycloalkyl, heteroaryl, cycloheteroalkyl, hydroxy, alkoxy, aryloxy, cyano, nitro, $NR^eR^f$, CHO, —$CO_2$alkyl, hydroxyaryl, aryloxyalkyl, $OCONR^eR^f$, $OCOR^e$, $OCOOR^eR^f$, —OCO-aryl, —OCO-heteroaryl, $CONR^eR^f$, $CO_2H$, $OCSOR^eR^f$, $CSNR^eR^f$ $NHCOR^i$, $NHCONR^eR^f$, $NHCSNR^eR^f$, $NHSO_pR^i$, —$SO_2NR^eR^f$, $NR^eSO_2NR^eR^f$, and $NR^eSO_pR^i$;
$R^7$ and $R^{11}$ are independently selected from hydrogen, aryl, alkyl, alkenyl, alkynyl, alkoxy, amino, substituted amino, alkoxyalkyl, $CO_2$alkyl, C(O)alkyl alkylaminoalkyl, dialkylaminoalkyl, heteroaryl, cycloheteroalkyl, heteroarylalkyl, cycloheteroalkylalkyl, cycloalkyl, and cycloalkylalkyl;
each occurrence of $R^4$, $R^5$, $R^6$, $R^7$, $R^8$, $R^9$, $R^{10}$, $R^{11}$ and $R^{12}$ is chosen independently; and
each of said A ring and said B ring contains at most one nitrogen ring atoms.

3. The compound as defined in claim 2, its stereoisomers thereof, or a pharmaceutically acceptable salt thereof, wherein:

$R_3$ is hydrogen or alkyl;
$R^a$ is selected from H, halogen, OH, $C_{1-4}$alkyl, CN, $NO_2$, $NH_2$, CHO, $CO_2$ alkyl, $CONR^eR^f$ or $CH_2NR^gR^h$; and
$R^b$ is selected from H, halo, OH, $C_{1-4}$alkyl, halogen, CN, $NO_2$, $NH_2$, CHO, $CO_2$ alkyl, $CONR^eR^f$ or $CH_2NR^eR^f$.

4. The compound as defined in claim 3, its stereoisomers thereof, or a pharmaceutically acceptable salt thereof, having a structure of formulae (IIA), (IIB) or (IIC):

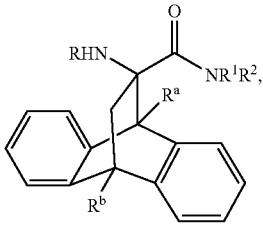

(IIA)

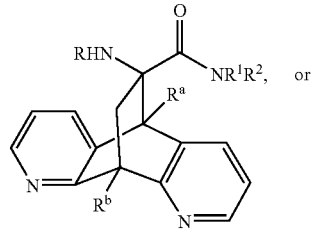

(IIB)

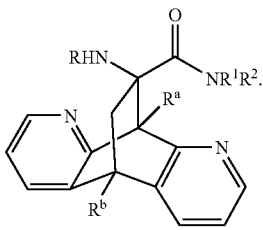

(IIC)

5. The compound as defined in claim 4, its stereoisomers thereof, or a pharmaceutically acceptable salt thereof, wherein $R^a$ is H, $CH_3$ or Cl and $R^b$ is H, $CH_3$, $NO_2$, or Cl.

6. The compound as defined in claim 5, its stereoisomers thereof, or a pharmaceutically acceptable salt thereof, wherein one of $R^1$ and $R^2$ is heteroaryl.

7. The compound as defined in claim 6, its stereoisomers thereof, or a pharmaceutically acceptable salt thereof, wherein one of $R^1$ and $R^2$ is selected from:

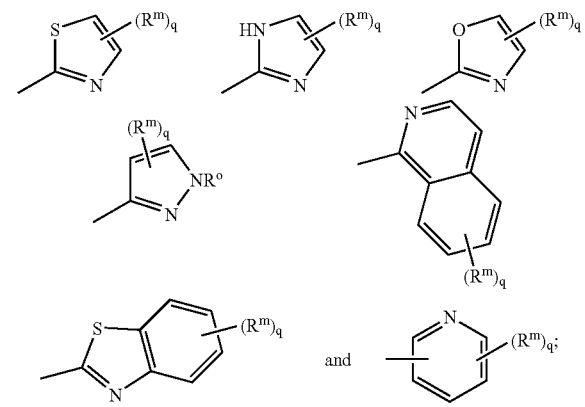

$R^m$ at each occurrence is independently selected from hydrogen, halogen, nitro, cyano, hydroxyl, alkoxy, —$CO_2$(alkyl), —C(O)N(alkyl)$_2$, alkyl, aryl and heteroaryl;

R° is hydrogen or alkyl; and q is 1 or 2.

8. A pharmaceutical composition comprising a compound as defined in claim 1 and a pharmaceutically acceptable carrier therefor.

9. A compound as defined in claim 7, its stereoisomers thereof, or a pharmaceutically acceptable salt thereof, having a structure of formulae (IIIA), (IIIB), (IIIC) or (IIID):

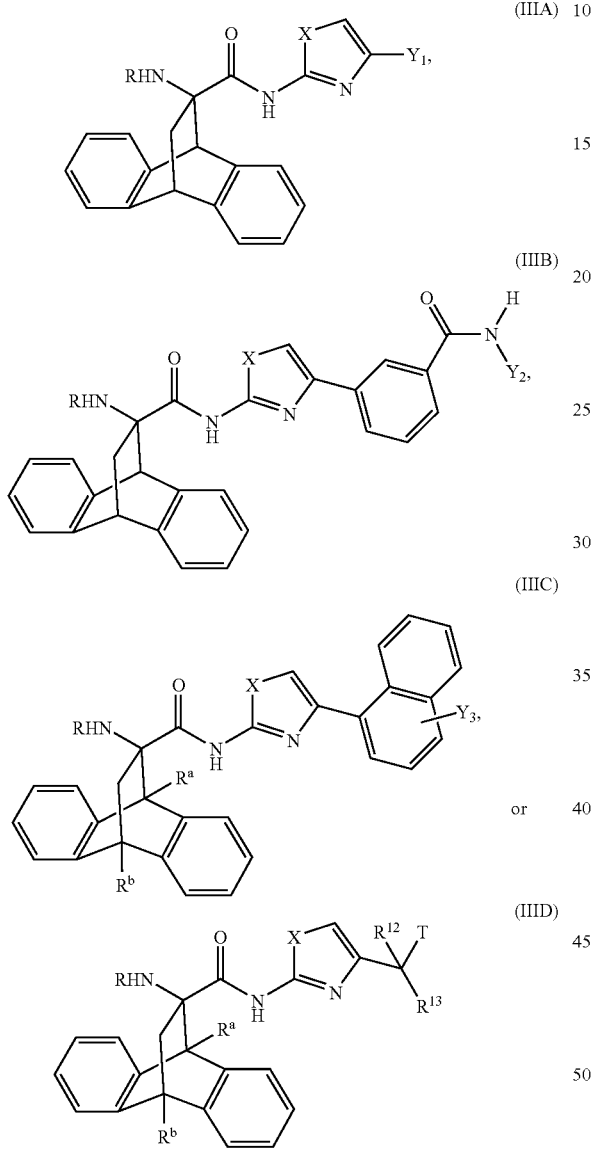

wherein:

$R^a$ is alkyl, halogen, hydrogen alkoxycarbonyl ($CO_2$ alkyl), nitro, or cyano;

$R^b$ is hydrogen, alkyl, halogen, $CO_2$alkyl, nitro, cyano, formyl, cycloheteroalkylcarbonyl, alkylaminoalkyl or amino, X is O, S, or NH;

$Y_1$ is hydrogen, halogen, nitro, cyano, hydroxy, alkoxy, or alkyl substituted with hydrogen, aryl or heteroaryl;

$Y_2$ is phenyl substituted by by 1 to 3 groups selected from hydrogen, halogen, nitro, cyano, hydroxy, alkoxy; alkyl, aryl and heteroaryl;

$Y_3$ is hydrogen, halogen, nitro, cyano, hydroxy, alkoxy; or alkyl;

T is a cycloalkyl, cycloalkenyl, heterocycloalkyl, aryl, or heteroaryl ring, each ring substituted by 0-1 $R^{14}$ and 0-4 $R^{15}$;

$R^{12}$ and $R^{13}$ are independently at each occurrence hydrogen, halogen, hydroxy, alkyl, alkenyl, alkynyl, alkoxy, cyano, nitro, $NR^eR^f$, or CHO provided that if M is $CR^m$, X is S, and either of $R^{12}$ and $R^{13}$ is alkyl, alkenyl, or alkynyl, then the other of $R^{12}$ and $R^{12}$ is not alkyl, alkenyl, or alkynyl;

or $R^{12}$ and $R^{13}$ combine to form =O or a double bond, wherein the double bond is substituted by hydrogen, aryl, alkyl, alkenyl, alkynyl, alkoxy, amino, substituted amino, alkoxyalkyl, alkylaminoalkyl, dialkylaminoalkyl, heteroaryl, cycloheteroalkyl, heteroarylalkyl, cycloheteroalkylalkyl, cycloalkyl, or cycloalkylalkyl;

$R^{14}$ and $R^{15}$ are, independently at each occurrence, hydrogen, halogen, hydroxy, alkyl, alkenyl, alkynyl, alkoxy, aryl, aryloxy, heteroaryl, cycloheteroalkyl, heteroarylalkyl, cycloheteroalkylalkyl, cyano, heteroarylaminocarboyl, cycloheteroalkylcarbonyl, cyanoalkyl, alkylaminoalkyl, hydroxyalkyl, hydroxyaryl, aryloxyalkyl, nitro, oxo, $NR^eR^f$, CHO, $CO_2$ alkyl, hydroxyaryl, aryloxyalkyl, $CONR^eR^f$, $CH_2NR^eR^f$, $CO_2H$, $CH_2OH$, $CH_2NHC(O)R^eR^f$, $NHCOR^g$, $NHCONR^eR^f$, $NHSO_pR^g$, $—SO_2NR^eR^f$, $NR^eSO_2NR^eR^f$, or $NR^eSO_pR^g$;

or $R^{14}$ and $R^{15}$ located on adjacent atoms can be taken together to form an optionally substituted cycloalkyl, aryl, heteroaryl, or cycloheteroalkyl ring.

10. A compound as defined in claim 9, its stereoisomers thereof, or a pharmaceutically acceptable salt thereof, wherein:

T is a phenyl, naphthyl, pyrimidyl, pyridinyl, pyridazinyl, piperazinyl, thiophenyl, thiazolyl, isoxazolyl, or imidazolyl ring; each ring of which is substituted by 0-4 $R^{15}$;

$R^{12}$ and $R^{23}$ are independently hydrogen, halogen, or hydroxy;

or $R^{12}$ and $R^{13}$ combine to form =O.

$R^{15}$ is hydrogen, $C_{1-4}$alkoxy; halogen, pyrimidine, isoxazole, pyrazole, or pyridine, where the $C_{1-4}$alkoxy; halogen, pyrimidine, isoxazole, pyrazole, or pyridine, groups are substituted by hydrogen, morpholinyl, $C_{1-4}$alkoxy, or $C_{1-4}$alkyl; and $R^b$ is selected from H, $CH_3$, Cl, Br, and CN.

11. A compound according to claim 10 having a structure of formula (IV):

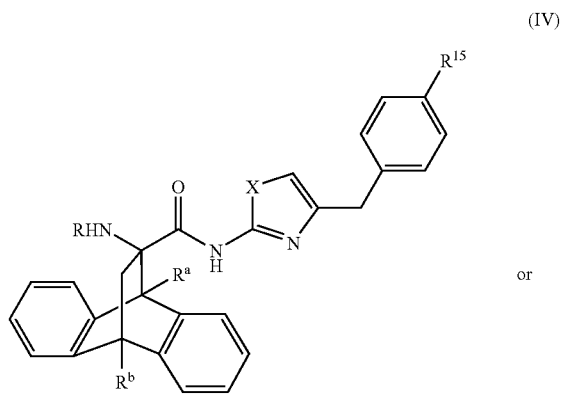

its stereoisomers thereof, or a pharmaceutically acceptable salt thereof, wherein:

X is S, or NH;

R is hydrogen or $C(O)C_{1-4}$alkyl; and

R[15] is C$_{1-4}$alkoxy; halogen, pyrimidine, isoxazole, pyrazole, or pyridine, where the C$_{1-4}$alkoxy; halogen, pyrimidine, isoxazole, pyrazole, or pyridine, groups are substituted by hydrogen, morpholinyl, C$_{1-4}$alkyl or C$_{1-4}$alkyl.

12. A compound according to claim 9 having a structure of formula (V):

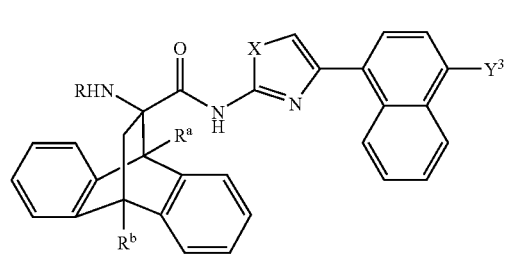
(V)

its stereoisomers thereof, or a pharmaceutically acceptable salt thereof, wherein:

X is S, or NH;
R is hydrogen or C(O)C$_{1-4}$alkyl; and
Y$^3$ is hydrogen, C$_{1-4}$alkyl, or halogen.

13. A compound as defined in claim 1 selected from the following:

(i)

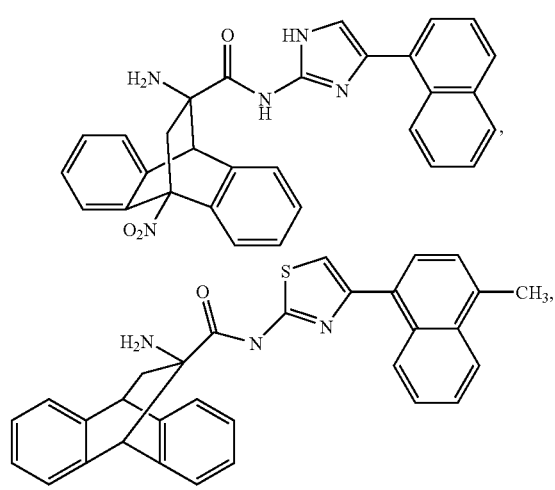

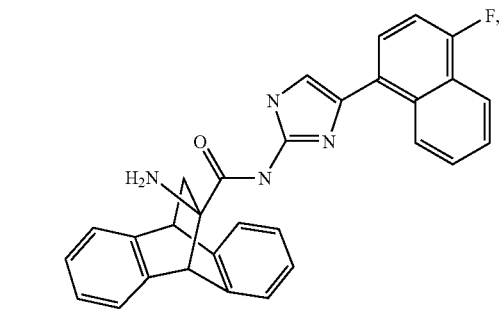

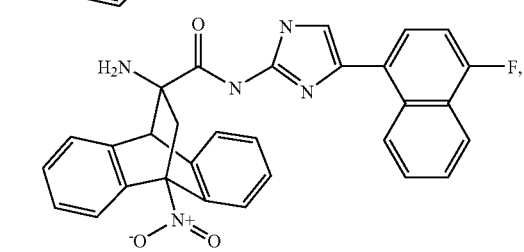

-continued

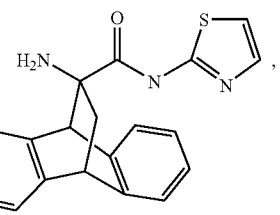

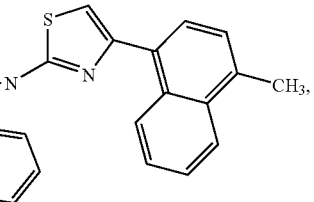

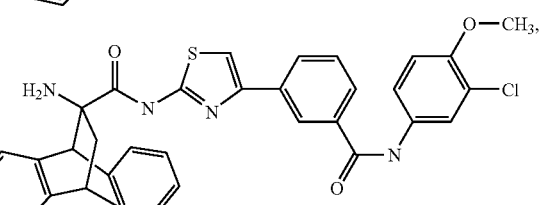

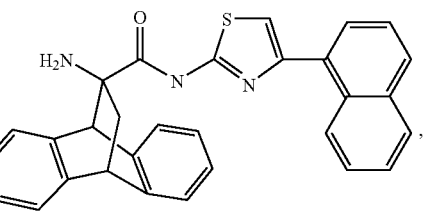

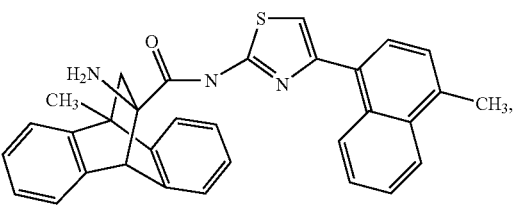

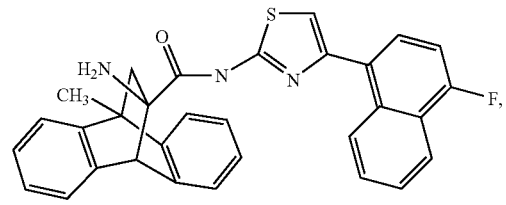

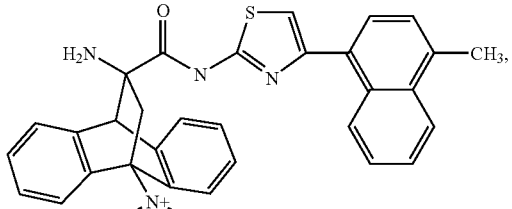

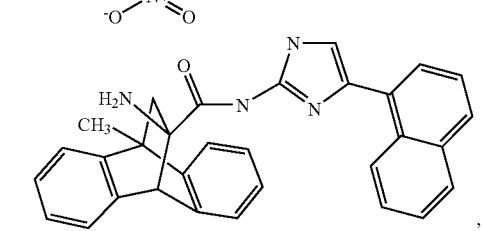

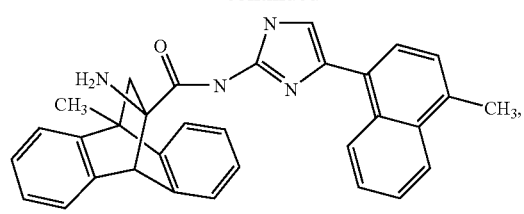
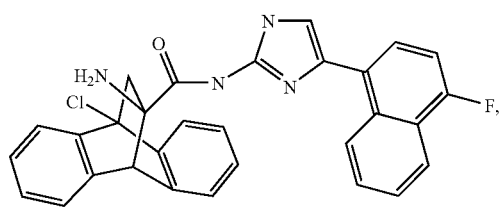
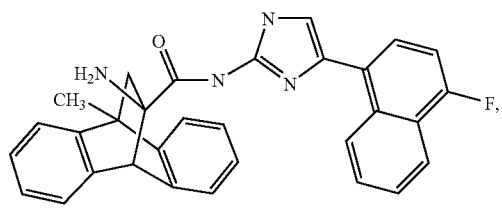
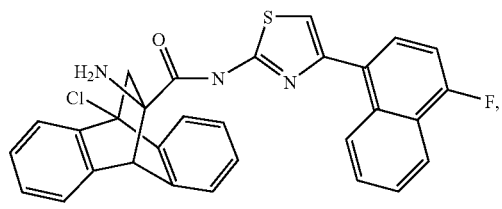
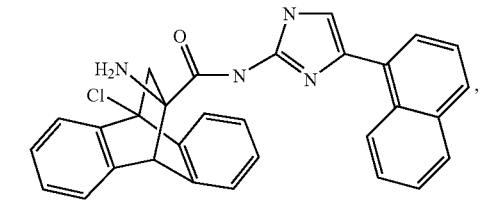
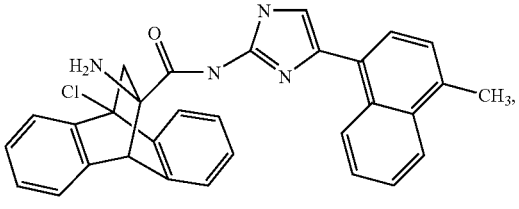
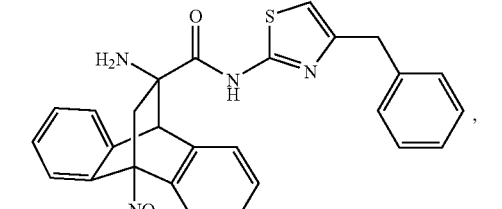
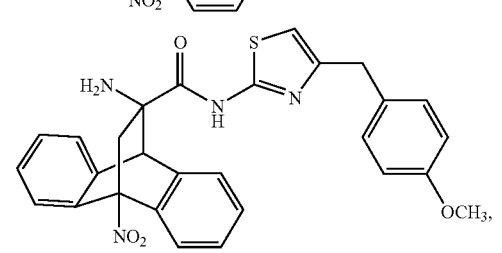
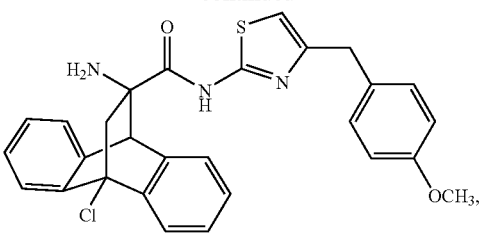
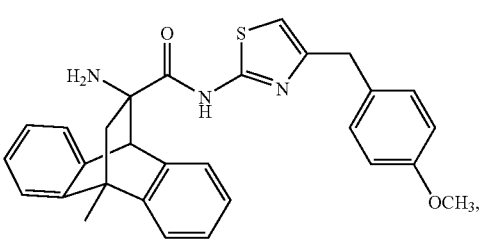
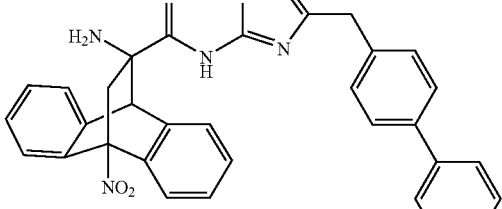
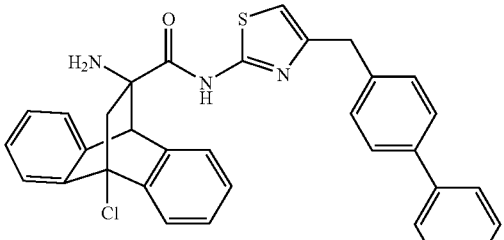
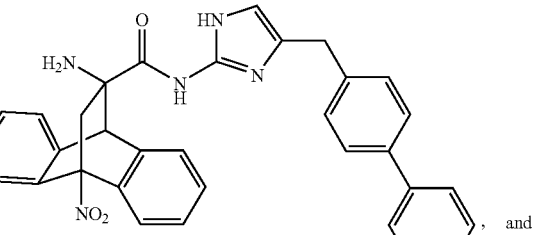
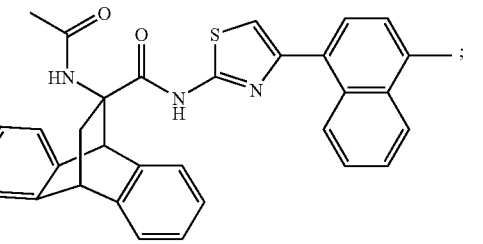
(ii) a stereoisomer of (i) thereof, or a pharmaceutically acceptable salt of (i), thereof.
* * * * *

UNITED STATES PATENT AND TRADEMARK OFFICE
CERTIFICATE OF CORRECTION

PATENT NO. : 7,326,728 B2
APPLICATION NO. : 11/035119
DATED : February 5, 2008
INVENTOR(S) : Bingwei Vera Yang et al.

It is certified that error appears in the above-identified patent and that said Letters Patent is hereby corrected as shown below:

On the Title Page:

Item (54), TITLE, change "NF-κβ" to -- NF-κB --.

Item (57), ABSTRACT, change "$CH^2NR^1R^2$" to -- $CH_2NR^1R^1$ --.

In the Specification:

Column 1, line 2, change "NF-κβ" to -- NF-κB --.

In the Claims:

Claim 1:

Column 58, lines 20 and 21, change "$S(O)_tR_3$, or $C(O)_tR_3$" to -- $S(O)_tR^3$, or $C(O)_tR^3$ --.

Column 58, line 36, change "heteroarylaminocarboyl" to
-- heteroarylaminocarbonyl --.

Column 58, line 64, change "$S(O)^tNR^1R^2$" to -- $S(O)_tNR^1R^2$ --.

Claim 2:

Column 59, line 46, change "$R^9$, $R^{10}$ and $R^{12}$" to -- $R^9$ and $R^{10}$ --.

Column 59, lines 52 to 54, change "$CSNR^eR^fNHCOR^i$, $NHCONR^eR^f$, $NHCSNR^eR^f$, $NHSO_pR^i$, —$SO_2NR^eR^f$, $NR^eSO_2NR^eR^f$, and $NR^eSO_pR^i$" to -- $NHCONR^eR^f$, $NHCSNR^eR^f$, —$SO_2NR^eR^f$, and $NR^eSO_2NR^eR^f$ --.

Column 59, lines 61 and 62, change "$R^{10}$, $R^{11}$ and $R^{12}$" to -- $R^{10}$ and $R^{11}$ --.

Column 59, line 64, change "atoms" to -- atom --.

Signed and Sealed this
Eleventh Day of January, 2011

David J. Kappos
*Director of the United States Patent and Trademark Office*

In the Claims:

Claim 3:
    Column 60, line 1, change "$R_3$" to -- $R^3$ --.

Claim 9:
    Column 61, line 63, change "by by" to -- by --.
    Column 62, lines 6 to 9, after "CHO", delete "provided that if M is $CR^m$, X is S, and either of $R^{12}$ and $R^{13}$ is alkyl, alkenyl, or alkynyl, then the other of $R^{12}$ and $R^{12}$ is not alkyl, alkenyl, or alkynyl".
    Column 62, lines 19 and 20, change "heteroarylaminocarboyl" to -- heteroarylaminocarbonyl --.
    Column 62, lines 24 and 25, change "$NHSO_pR^g$, —$SO_2NR^eR^f$, $NR^eSO_2NR^eR^f$, or $NR^eSO_pR^g$;" to -- —$SO_2NR^eR^f$ and $NR^eSO_2NR^eR^f$; --.

Claim 10:
    Column 62, line 36, change "$R^{23}$" to -- $R^{13}$ --.
    Column 62, line 38, after "=C", change "." to -- ; --.